United States Patent
Alverdy

(10) Patent No.: US 9,937,199 B2
(45) Date of Patent: Apr. 10, 2018

(54) MATERIALS AND METHODS FOR PREVENTING AND TREATING ANASTOMOTIC LEAKS

(71) Applicants: THE UNIVERSITY OF CHICAGO, Chicago, IL (US); John C. Alverdy, Glenview, IL (US)

(72) Inventor: John C. Alverdy, Glenview, IL (US)

(73) Assignee: THE UNIVERSITY OF CHICAGO, Chicago, IL (US)

(*) Notice: Subject to any disclaimer, the term of this patent is extended or adjusted under 35 U.S.C. 154(b) by 0 days.

(21) Appl. No.: 14/421,762

(22) PCT Filed: Mar. 14, 2013

(86) PCT No.: PCT/US2013/031684
§ 371 (c)(1),
(2) Date: Feb. 13, 2015

(87) PCT Pub. No.: WO2014/028052
PCT Pub. Date: Feb. 20, 2014

(65) Prior Publication Data
US 2015/0297634 A1    Oct. 22, 2015

Related U.S. Application Data

(60) Provisional application No. 61/684,641, filed on Aug. 17, 2012.

(51) Int. Cl.
| | | |
|---|---|---|
| A61K 31/765 | (2006.01) | |
| A61K 33/42 | (2006.01) | |
| A61K 31/66 | (2006.01) | |
| A61L 31/02 | (2006.01) | |
| A61L 31/06 | (2006.01) | |
| A61L 31/16 | (2006.01) | |

(Continued)

(52) U.S. Cl.
CPC ............ *A61K 31/765* (2013.01); *A61K 31/66* (2013.01); *A61K 31/77* (2013.01); *A61K 33/42* (2013.01); *A61L 31/028* (2013.01); *A61L 31/06* (2013.01); *A61L 31/16* (2013.01); *A61B 17/11* (2013.01); *A61L 2300/112* (2013.01)

(58) Field of Classification Search
CPC .................................................. A61K 2300/00
See application file for complete search history.

(56) References Cited

U.S. PATENT DOCUMENTS

2009/0186949 A1   7/2009  Alverdy et al.

OTHER PUBLICATIONS

Platell et al. Randomized Clinical Trial of Bowl Preparations With a Single Phosphate Enema or Polyethylene Glycol. Nov. 2005.*

(Continued)

*Primary Examiner* — Adam C Milligan
*Assistant Examiner* — Sarah Alawadi
(74) *Attorney, Agent, or Firm* — Marshall, Gerstein & Borun LLP

(57) ABSTRACT

Materials and methods for preventing and treating anastomotic leaks are disclosed. Data establishes that pathogenic microbes interfere with establishing epithelial cell barriers in anastomoses and, more generally, with the reconnection of any two portions of like or different tissues comprising epithelia. Suitable prophylactic and therapeutic composition comprise, e.g., a phosphorylated high molecular weight polyethylene glycol compound.

13 Claims, 17 Drawing Sheets

(51) Int. Cl.
*A61K 31/77* (2006.01)
*A61B 17/11* (2006.01)

(56) References Cited

OTHER PUBLICATIONS

Glycoprep Product Information Feb. 2001.*
Menotti. Wood and Polyethylene Glycol Treatment 2012).*
Long et al. Depletion of Intestinal Phosphate After Operative Injury Activates The Virulence of P. aeruginosa causing Lethal Gut-Derived Sepsis. 2008.*
Cohen et al. Quantities, Units and Symbols in Physical Chemistry. 2007.*
Akiyoshi et al., Incidence of and risk factors for anastomotic leakage after laparoscopic anterior resection with intracorporeal rectal transection and double-stapling technique anastomosis for rectal cancer, *Am. J. Surg.*, 202:259-64 (2011).
Alanezi et al., Mortality secondary to esophageal anastomotic leak, *Ann. Thorac. Cardiovasc. Surg.*, 10:71-5 (2004).
Aziz et al., The RAST Server: rapid annotations using subsystems technology, *BMC Genomics*, 9:75 (2008).
Blewett et al., Anastomotic leaks after esophagectomy for esophageal cancer: a comparison of thoracic and cervical anastomoses, *Ann. Thorac. Cardiovasc. Surg.*, 7:75-8 (2001).
Chevreux et al., Using the miraEST assembler for reliable and automated mRNA transcript assembly and SNP detection in sequenced ESTs, *Genome Res.*, 14:1147-59 (2004).
Chiang et al., Protective effects of high-molecular weight Polyethylene Glycol (PEG) in human lung endothelial cell barrier regulation: Role of actin cytoskeletal rearrangement, *Microvass. Res.*, 77:174-186 (2008).
Choi et al., Risk factors for anastomotic leakage after laparoscopic rectal resection, *J. Korean Soc. Coloproctol.*, 26:265-73 (2010).
Cohen et al., Healing of ischemic colonic anastomoses in the rat: role of antibiotic preparation, *Surgery*, 97:443-6 (1985).
Cohn et al., Antibiotic protection of colon anastomoses, *Ann. Surg.*, 141:707-17 (1955).
GenBank Accesion No. AJ007825, Pseudomonas aeruginosa mexT gene, Apr. 14 2005.
Hyman et al., Anastomotic leaks after intestinal anastomosis: it's later than you think, *Ann. Surg.*, 245:254-8 (2007).
International Search Report and Written Opinion of the International Searching Authority, PCT/US2013/031684, dated Nov. 19, 2013.
International Preliminary Report on Patentability, PCT/US2013/031684, dated Feb. 17, 2015.
Jin et al., MexT regulates the type III secretion system through MexS and PtrC in Pseudomonas aeruginosa, *J. Bacteriol.*, 193:399-410 (2011).
Klockgether et al., Genome diversity of Pseudomonas aeruginosa PA01 laboratory strains, *J. Bacteriol.*, 192:1113-21.
Kohler et al., Characterization of MexT, the regulator of the MexE-MexF-OprN multidrug efflux system of Pseudomonas aeruginosa, *J. Bacteriol.*, 181:6300-5 (1999).
Kohler et al., Overexpression of the MexEF-OprN multidrug efflux system affects cell-to-cell signaling in Pseudomonas aeruginosa, *J. Bacteriol.*, 183:5213-22 (2001).
Lesic et al., Use of the lambda Red recombinase system to rapidly generate mutants in Pseudomonas aeruginosa, *BMC Mol. Biol.*, 9:20 (2008).
Lin et al., The influence of fecal diversion and anastomotic leakage on survival after resection of rectal cancer, *J. Gastrointest. Surg.*, 15:225161 (2011).

Maseda et al., Variation of the mexT gene, a regulator of the MexEF-oprN efflux pump expression in wild-type strains of Pseudomonas aeruginosa, *FEMS Microbiol. Lett.*, 192:107-12 (2000).
Maseda et al., Transcriptional regulation of the mexEF-oprN multidrug efflux pump operon by MexT and an unidentified repressor in nfxC-type mutant of Pseudomonas aeruginosa, *FEMS Microbiol. Lett.*, 311:36-43 (2010).
Merkel et al., Locoregional recurrence in patients with anastomotic leakage after anterior resection for rectal carcinoma, *Colorectal Dis.*, 3:154-60 (2001).
Pace et al., Synthesis and reactivity of high-molecular-mass phosphorylated poly(ethylene glycol), *Reactive and Functional Polymers*, 41(1-3):141-8 (1999).
Ricciardi et al., Anastomotic leak testing after colorectal resection: what are the data? *Arch. Surg.*, 144:407-11 (2009).
Romanowski et al., Prevention of siderophore- mediated gut-derived sepsis due to P. aeruginosa can be achieved without iron provision by maintaining local phosphate abundance: role of pH, *BMC Microbiol.*, 11: 212 (2011).
Roos et al., Randomized clinical trial of perioperative selective decontamination of the digestive tract versus placebo in elective gastrointestinal surgery, *Br. J. Surg.*, 98:1365-72 (2011).
Schardey et al., The prevention of anastomotic leakage after total gastrectomy with local decontamination. A prospective, randomized, double-blind placebo-controlled multicenter trial, *Ann. Surg.*, 225:172-80 (1997).
Schardey et al., Bacteria: a major pathogenic factor for anastomotic insufficiency, *Antimicrob. Agents Chemother.*, 38:2564-7 (1994).
Seal et al., The molecular Koch's postulates and surgical infection: a view forward, *Surgery*, 147:757-65 (2010).
Shogan et al., Cues Present at Anastomotic Leak Sites Induce a Stable mexT Mutation in Pseudomonas Aeruginosa Causing Enhanced Tissue Destroying Capacity, Thirty-second Annual Meeting of the Surgical Infection Society, section 0-10 found on S-11 (2012).
Stover et al., Complete genome sequence of Pseudomonas aeruginosa PA01, an opportunistic pathogen, *Nature*, 406:959-64 (2000).
Tian et al., Transcriptome profiling defines a novel regulon modulated by the LysR-type transcriptional regulator MexT in Pseudomonas aeruginosa, *Nucleic Acids Res.*, 37:7546-59 (2009).
Tian et al., MexT modulates virulence determinants in Pseudomonas aeruginosa independent of the MexEF-OprN efflux pump, *Microb. Pathog.*, 47:237-41 (2009).
Tremblay et al., Improving the reproducibility of Pseudomonas aeruginosa swarming motility assays, J. Basic Microbiol., 48:509-15 (2008).
Valuckaite et al., Oral Peg 1520 protects the intestine against radiation: role of lipid rafts, *Am. J. Physiol. Gastrointest Liver Physiol.*, 297:G1041-52 (2009).
Wu et al., Recognition of host immune activation by Pseudomonas aeruginosa, *Science*, 309:74-7 (2005).
Zaborin et al., Pseudomonas aeruginosa overrides the virulence inducing effect of opioids when it senses an abundance of phosphate, *PLoS One*,7:e34883 (2012).
Zaborin et al., Red death in Caenorhabditis elegans caused by Pseudomonas aeruginosa PA01, *Proc. Natl. Acad. Sci., USA*, 106:6327-32 (2009).
Zaborina et al., Identification of multi-drug resistant Pseudomonas aeruginosa clinical isolates that are highly disruptive to the intestinal epithelial barrier, *Ann. Clin. Microbiol. Antimicrob.*, 5:14 (2006).
Zaborina et al., Dynorphin activates quorum sensing quinolone signaling in Pseudomonas aeruginosa, *PLoS Pathog.*, 3:e35 (2007).
Zaoui et al., An orphan sensor kinase controls quinolone signal production via MexT in Pseudomonas aeruginosa, *Mol. Microbiol.*, 83:536-47.

* cited by examiner

Figure 12A

```
c atg aac cga aac gac ctg cgc cgc gtc gat ctg aac ctg ctg atc gtg         49
  Met Asn Arg Asn Asp Leu Arg Arg Val Asp Leu Asn Leu Leu Ile Val
  1               5                   10                  15 ttc gag acc ctg atg cac gaa cgc agc gtg acc cgc gcc gca gag aaa           97
Phe Glu Thr Leu Met His Glu Arg Ser Val Thr Arg Ala Ala Glu Lys
                    20                  25                  30 ctg ttc ctc ggc cag ccg gcc atc agc gcc gcg ctg tcg cgc ctg cgc          145
Leu Phe Leu Gly Gln Pro Ala Ile Ser Ala Ala Leu Ser Arg Leu Arg
                35                  40                  45 acg ctg ttc gac gac ccg ctg ttc gtc cgt acc gga cgc agc atg gag          193
Thr Leu Phe Asp Asp Pro Leu Phe Val Arg Thr Gly Arg Ser Met Glu
    50                  55                  60 ccc acc gcg cga gcc cag gaa atc ttc gcc cac ctg tcg ccg gcg ctg          241
Pro Thr Ala Arg Ala Gln Glu Ile Phe Ala His Leu Ser Pro Ala Leu
65                  70                  75                  80 gat tcc atc tcc acc gcc atg agt cgc gcc agc gag ttc gat ccg gcg          289
Asp Ser Ile Ser Thr Ala Met Ser Arg Ala Ser Glu Phe Asp Pro Ala
                    85                  90                  95 acc agc acc gcg gtg ttc cgc atc ggc ctt tcc gac gac gtc gag ttc          337
Thr Ser Thr Ala Val Phe Arg Ile Gly Leu Ser Asp Asp Val Glu Phe
                100                 105                 110 ggc ctg ttg ccg ccc ctg ctc cgc cgc ctg cgc gcg gag gcg ccg ggg          385
Gly Leu Leu Pro Pro Leu Leu Arg Arg Leu Arg Ala Glu Ala Pro Gly
            115                 120                 125 atc gtc ctc gtc gtg cgc cgc gcc aac tat cta ttg atg ccg aac ctg          433
Ile Val Leu Val Val Arg Arg Ala Asn Tyr Leu Leu Met Pro Asn Leu
        130                 135                 140 ctg gcc tcg ggg gag atc tcg gtg ggc gtc agc tac acc gac gaa ctg          481
Leu Ala Ser Gly Glu Ile Ser Val Gly Val Ser Tyr Thr Asp Glu Leu
145                 150                 155                 160
```

Figure 12 B

```
ccg gcc aac gcc aag cgc aag acc gtg cgc cgc agc aag ccg aag atc        529
Pro Ala Asn Ala Lys Arg Lys Thr Val Arg Arg Ser Lys Pro Lys Ile
            165             170             175 ctc cgc gcc gac tcc gcg ccc ggc cag ctg acc ctc gac gac tat tgc        577
Leu Arg Ala Asp Ser Ala Pro Gly Gln Leu Thr Leu Asp Asp Tyr Cys
            180             185             190 gcg cga ccg cac gcg ctg gtg tcc ttc gcc ggc gac ctc agc ggc ttc        625
Ala Arg Pro His Ala Leu Val Ser Phe Ala Gly Asp Leu Ser Gly Phe
            195             200             205 gtc gac gag gag ctg gaa aaa ttc ggc cgc aag cgc aag gtg gtc ctg        673
Val Asp Glu Glu Leu Glu Lys Phe Gly Arg Lys Arg Lys Val Val Leu
            210             215             220 gcg gtg ccg cag ttc aac ggc ctc ggc acc ctc ctg gcc ggc acc gac        721
Ala Val Pro Gln Phe Asn Gly Leu Gly Thr Leu Leu Ala Gly Thr Asp
225             230             235             240 atc atc gcc acc gtg ccc gac tac gcc gcc cag gcg ctg atc gcc gcc        769
Ile Ile Ala Thr Val Pro Asp Tyr Ala Ala Gln Ala Leu Ile Ala Ala
            245             250             255 ggc ggc cta cgc gcc gag gac cca ccg ttc gag acc cgg gcc ttc gaa        817
Gly Gly Leu Arg Ala Glu Asp Pro Pro Phe Glu Thr Arg Ala Phe Glu
            260             265             270 ctg tcg atg gct tgg cgc ggc gcc cag gac aac gat ccg gcc gaa cgc        865
Leu Ser Met Ala Trp Arg Gly Ala Gln Asp Asn Asp Pro Ala Glu Arg
            275             280             285 tgg ctg cgc tcg cgg atc agc atg ttc atc ggc gat ccg gac agt ctc        913
Trp Leu Arg Ser Arg Ile Ser Met Phe Ile Gly Asp Pro Asp Ser Leu
            290             295             300 tga                                                                     916
```

MATERIALS AND METHODS FOR PREVENTING AND TREATING ANASTOMOTIC LEAKS

CROSS REFERENCE TO RELATED APPLICATIONS

This application claims the priority benefit under 35 U.S.C. § 119(e) of U.S. Provisional Application No. 61/684,641, filed Aug. 17, 2012, the disclosure of which is incorporated herein by reference in its entirety.

STATEMENT OF GOVERNMENT INTEREST

This invention was made with government support under Grant Number RO1-GM062344-12, awarded by the National Institutes of Health (NIH), and under Grant Number DE-AC02-06CH11357 awarded by the U.S. Department of Energy (DOE). The government has certain rights in the invention.

FIELD OF THE INVENTION

The disclosure relates to the treatment of medical conditions generally, and more specifically to the prevention and treatment of anastomotic leakage, e.g., in the intestine.

BACKGROUND

When patients undergo removal (resection) and re-connection (anastomosis) of a segment or whole portion of the gastrointestinal tract, a significant number will develop anastomotic leaks despite being operated on by highly qualified surgeons in high-volume centers. Anastomotic leaks cause major long-term bowel dysfunction (incontinence), high cancer recurrence rates, decreased long term cancer survival, and sepsis-related deaths. The cause of anastomotic leaks remains unknown.

Cohn first proposed in 1955 that the microbial content of the gut plays a central role in the pathogenesis of anastomotic leak [4]. In his experiments, dogs were subjected to colon anastomosis and division of the mesenteric blood vessels to cause ischemia and delayed healing. One group was administered intraluminal antibiotics (tetracycline directly into the bowel via an indwelling catheter) and the other saline. Antibiotic treated dogs demonstrated complete anastomotic healing and recovery whereas those administered saline developed major leakage with peritonitis and death. Shardley was the first to suggest that *P. aeruginosa* might play a causative role in anastomotic leak [5], and performed the first randomized prospective placebo blinded trial with antibiotics confirming a role for microbes in human anastomotic leak [6]. Yet despite this and other similar compelling observations, a microbial mechanism for anastomotic leak is generally not accepted and, around the world, anastomotic leak is posited to be primarily a problem of poor technique and/or poor wound healing [7-9].

Accordingly, a need persists in the art for increased understanding of anastomotic leak, and for methods of preventing and treating diseases, disorders and conditions associated with anastomotic leak.

SUMMARY

Disclosed herein is evidence that intestinal *P. aeruginosa*, now emerging as a frequent commensal in hospitalized patients following surgery, undergoes a stable genetic mutation at the site of tissue injury (i.e., anastomosis) that results in its transformation to a tissue destructive phenotype capable of causing anastomotic leak. Sequence analysis of *P. aeruginosa* recovered from the anastomosis site demonstrated a SNP in the mexT gene that confers swarming capacity, enhanced collagenase activity, and an epithelial disruption phenotype. The enhanced virulence phenotype was inducible by incubating the original strain with ex vivo anastomotic tissues, demonstrating the importance of the in vivo environment and tissue injury for the expression of the tissue-destroying phenotype. Use of polyethylene glycol polymers with added phosphate suppressed virulence in *P. aeruginosa* without affecting its growth, prevented its virulence transformation and prevented anastomotic leak.

An aspect of the disclosure is drawn to a method of treating anastomotic leakage comprising administering a therapeutically effective amount of a composition comprising a compound selected from the group consisting of high molecular weight polyethylene glycol and inorganic phosphorus. In some embodiments, the compound is high molecular weight polyethylene glycol, such as phosphorylated high molecular weight polyethylene glycol, e.g., high molecular weight PEG phosphate. Contemplated are implementations of the method wherein the anastomotic leakage is in the intestine or in the esophagus. Suitable compositions comprise high molecular weight PEG that has an average molecular weight selected from the group consisting of at least 8,000 9,000, 10,000, 11,000, 12,000, 13,000, 14,0000, 15,000 and 15,000 to 20,000 daltons. In some embodiments, a cause of the anastomotic leakage is a virulent microbe, such as virulent *Pseudomonas aeruginosa*. In some particular embodiments, the virulent *Pseudomonas aeruginosa* has a loss-of-function mutation in mexT. In some embodiments, the mutation in mexT is a single nucleotide polymorphism, such as the C→A mutation at position 135 of mexT (compare the C at position 135 of mexT-P1 (SEQ ID NO:1) with the A at position 135 of mexT-P2 (SEQ ID NO:3)).

Another aspect of the disclosure is a method of preventing anastomotic leakage comprising administering a prophylactically effective amount of a composition comprising a compound selected from the group consisting of high molecular weight polyethylene glycol and inorganic phosphorus to a subject known to have or at risk of having an anastomosis. In some embodiments, the compound is high molecular weight polyethylene glycol, such as phosphorylated high molecular weight polyethylene glycol. The method is suitable for preventing or treating a variety of anastomoses, including but not limited to intestinal and esophageal anastomoses. In some embodiments, the high molecular weight PEG has an average molecular weight selected from the group consisting of at least 8,000 daltons, at least 10,000 daltons, at least 11,000 daltons, at least 12,000 daltons, at least 15,000 daltons and at least 15,000 to 20,000 daltons. In particular embodiments, the high molecular weight PEG has an average molecular weight of at least 15,000 to 20,000 daltons. In some embodiments, the composition comprises an inorganic phosphorus compound, wherein the inorganic phosphorus is phosphate.

Particular aspects of the disclosure are described in the following enumerated paragraphs.

1. A method of treating anastomotic leakage comprising administering a therapeutically effective amount of a composition comprising a compound selected from the group consisting of high molecular weight polyethylene glycol and inorganic phosphorus.

2. The method according to paragraph 1 wherein the compound is high molecular weight polyethylene glycol.

3. The method according to paragraph 1 wherein the compound is phosphorylated high molecular weight polyethylene glycol.

4. The method according to paragraph 1 wherein the anastomotic leakage is in the intestine.

5. The method according to paragraph 1 wherein the anastomotic leakage is in the esophagus.

6. The method according to paragraph 1 wherein the high molecular weight PEG has an average molecular weight selected from the group consisting of at least 8,000 daltons, at least 10,000 daltons, at least 11,000 daltons, at least 12,000 daltons, at least 15,000 daltons and at least 15,000 to 20,000 daltons.

7. The method according to paragraph 6 wherein the high molecular weight PEG has an average molecular weight of 15,000 to 20,000 daltons.

8. The method according to paragraph 1 wherein the inorganic phosphorus is phosphate.

9. The method according to paragraph 1 wherein a cause of the anastomotic leakage is a virulent microbe.

10. The method according to paragraph 9 wherein the microbe is virulent *Pseudomonas aeruginosa*.

11. The method according to paragraph 10 wherein the virulent *Pseudomonas aeruginosa* has a loss-of-function mutation in mexT.

12. The method according to paragraph 11 wherein the mutation in mexT is a single nucleotide polymorphism at position 135 of SEQ ID NO:3.

13. A method of preventing anastomotic leakage comprising administering a prophylactically effective amount of a composition comprising a compound selected from the group consisting of high molecular weight polyethylene glycol and inorganic phosphorus to a subject known to have or at risk of having an anastomosis.

14. The method according to paragraph 13 wherein the compound is high molecular weight polyethylene glycol.

15. The method according to paragraph 13 wherein the compound is phosphorylated high molecular weight polyethylene glycol.

16. The method according to paragraph 13 wherein the anastomosis is an intestinal anastomosis.

17. The method according to paragraph 13 wherein the anastomosis is an esophageal anastomosis.

18. The method according to paragraph 13 wherein the high molecular weight PEG has an average molecular weight selected from the group consisting of at least 8,000 daltons, at least 10,000 daltons, at least 11,000 daltons, at least 12,000 daltons, at least 15,000 daltons and at least 15,000 to 20,000 daltons.

19. The method according to paragraph 18 wherein the high molecular weight PEG has an average molecular weight of at least 15,000 to 20,000 daltons.

20. The method according to paragraph 13 wherein the inorganic phosphorus is phosphate.

Other features and advantages of the disclosure will become apparent from the following detailed description, including the drawing. It should be understood, however, that the detailed description and the specific examples, while indicating preferred embodiments, are provided for illustration only, because various changes and modifications within the spirit and scope of the invention will become apparent to those skilled in the art from the detailed description.

BRIEF DESCRIPTION OF THE DRAWING

FIGS. 12A-12B. Polynucleotide and amino acid sequences of MexT. The polynucleotide sequence of the coding region of the mexT gene of Pseudomonas aeruginosa strain P1 is presented, with the sequence grouped into codons using the expressed reading frame. The C at position 135 (SEQ ID NO:1) is mutated to an "A" in the P2 strain described herein, creating an in-frame stop codon. Beneath each row of polynucleotide sequence is the encoded amino acid sequence (SEQ ID NO:2) presented using the three-letter amino acid code.

DETAILED DESCRIPTION

Figure 1:
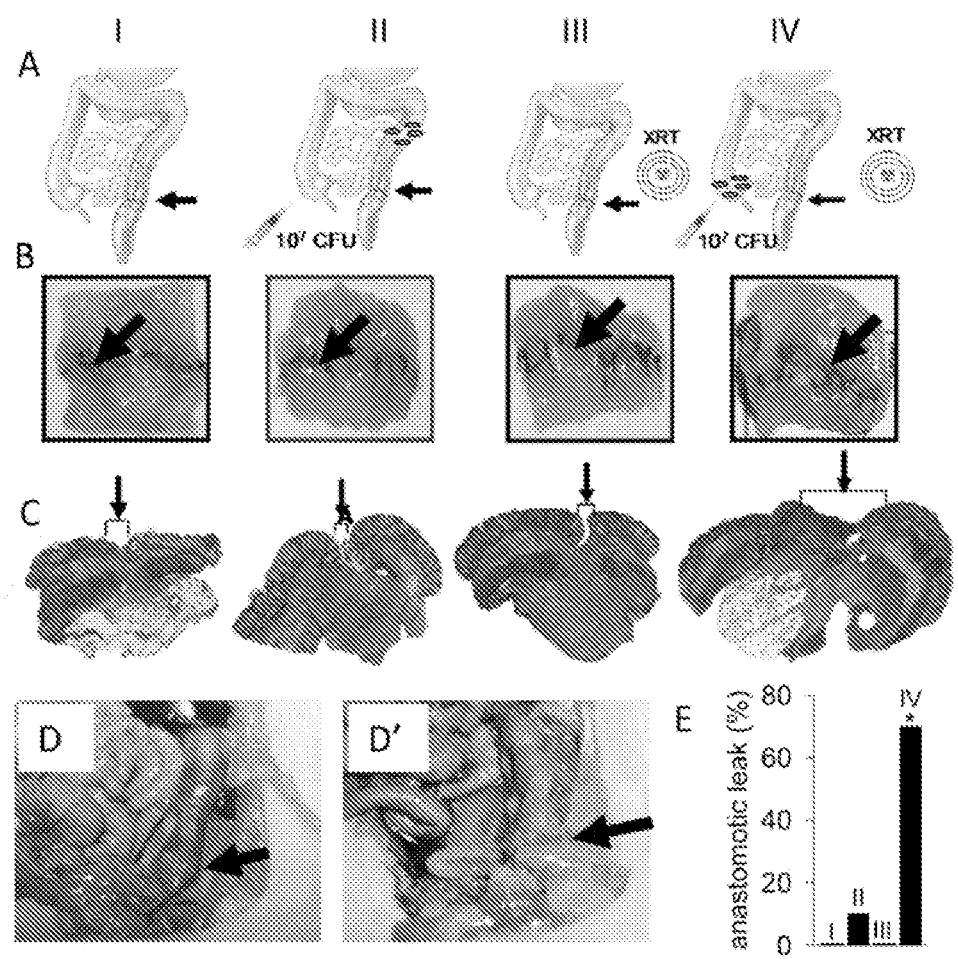
FIG. 1. Anastomotic leak in rats exposed to pre-operative radiation and intestinal *P. aeruginosa*. (A) Sketch of anastomosis model and treatment groups. Treatment groups: I, anastomosis only; II, anastomosis+cecal injection of *P. aeruginosa* MPAO1, $10^7$ CFU; III, radiation+anastomosis; IV, radiation+anastomosis+cecal injection of *P. aeruginosa* MPAO1 ($10^7$ CFU). Black arrows indicate the anastomotic site. (B) Excised and exposed suture lines of anastomotic sites. All suture lines are grossly intact except for group IV where ulceration/dehiscence is noted by the black arrow. (C) hematoxylin & eosin (i.e., H&E) staining of anastomotic tissues. Arrows and brackets indicate width of tissue apposition at suture line. (D, D', E) Methylene blue assessment of anastomotic integrity demonstrating rare to no leaks in groups I-III (D) and gross extravasation in group IV (D'). Arrows indicate the site of anastomosis. (E) Incidence of anastomotic leak between groups. n=12 (group I), n=16 (group II), n=9 (group III), n=18 (group IV), *p<0.01.

The most feared complication following intestinal resection is anastomotic leakage. In high risk areas (i.e., esophagus/rectum) where neoadjuvant chemoradiation is used, the incidence of anastomotic leaks remains unacceptably high (about 10%), even when performed by specialist surgeons in high-volume centers. The experiments disclosed herein tested the hypothesis that anastomotic leakage develops when pathogens colonizing anastomotic sites become transformed in vivo to express a tissue-destroying phenotype.

A model of anastomotic leak was developed in which rats were exposed to pre-operative radiation as in cancer surgery, underwent distal colon resection and then were intestinally inoculated with Pseudomonas aeruginosa, a common colonizer of the radiated intestine. Results demonstrated that intestinal tissues exposed to preoperative radiation developed a significant incidence of anastomotic leak (>60%; p<0.01) when colonized by P. aeruginosa, compared to radiated tissues alone (0%). Phenotype analysis comparing the original inoculating strain (MPAO1, termed P1) and the strain retrieved from leaking anastomotic tissues (termed P2) demonstrated that P2 was altered in pyocyanin production and displayed enhanced collagenase activity, high swarming motility, and a destructive phenotype against cultured intestinal epithelial cells (i.e., apoptosis, barrier function, cytolysis). Comparative genotype analysis between P1 and P2 revealed a single nucleotide polymorphism (SNP) mutation in the mexT gene that led to a stop codon resulting in a non-functional truncated protein. Replacement of the mutated mexT gene in P2 with mexT from the original parental strain P1 led to reversion of P2 to the P1 phenotype. No spontaneous transformation was detected during 20 passages in TSB media. Also disclosed herein is a virulence-suppressing compound, PEG/Pi, which prevented P. aeruginosa transformation to the tissue-destructive phenotype and prevented anastomotic leak in rats. This work demonstrates that in vivo transformation of microbial pathogens to a tissue-destroying phenotype may have important implications in the pathogenesis of anastomotic leak.

Despite decades of refinements in technique, the development of ergonomic stapling devices, and the emergence of high-volume specialized surgeons working in high-volume centers, anastomotic leaks remain a real and present danger to patients. This is particularly evident in high risk areas of the gastrointestinal tract such as the esophagus and rectum, where the incidence of leak persists at 10% and paradoxically appears to be increasing in incidence. Results from the present study extend the observations by Cohn nearly 60 years ago [4] and later confirmed by Schardey in 1994 [5] and introduce a model which conforms to the molecular Koch's postulates that microbial phenotype, rather than microbial presence alone, plays a role in the tissue disruption that characterizes anastomotic leak. Placing this finding in the context of the practice of high-risk gastrointestinal surgery is important as surgeons are operating on more complex and older patients who often have received adjunctive chemotherapy and radiation either before or after intestinal resection. The promiscuous use of antibiotics may also contribute to colonization by more pathogenic strains of bacteria at anastomotic sites, that when properly cued by host elements at the site of tissue injury, can become transformed to express a tissue destructive phenotype. Such dynamic microbial virulence regulation that may be dependent on both spatial and regional context may explain, in part, the relative difficulty in predicting those at risk for anastomotic leak.

The ability of P1 to transform to P2 and acquire high-swarming and enhanced ability to degrade collagen are undoubtedly important assets for P. aeruginosa to acquire as a mechanism to cause full thickness loss of anastomotic integrity. The data generated by the present study, however, are insufficient to determine the causative link between the P2 phenotype and anastomotic leak per se. Although anastomotic tissues, with or without exposure to radiation, induced the P2 phenotype, P2 may only exert its full potential to cause leakage when it is further cued by radiated tissues, a hypothesis that currently cannot be tested in vitro. Evidence for this is our recent observation that P. aeruginosa virulence is activated by soluble factors released from radiated intestinal epithelial cells. There are, however, major technical challenges to causally linking the P2 phenotype to anastomotic leak. P2 was introduced into the cecum of rats with anastomotic construction but without radiation and it did not cause anastomotic leak. In contrast to radiated rats, non-radiated rats maintain a normal microbiota and intact mucus layer, which may shield against the virulence effects of the P2 phenotype. Additionally, once P2 is afforded the opportunity to adhere to anastomotic tissues in radiated mice, contact-dependent host tissue factors may induce transcriptional changes in P2 that then confer an even more invasive tissue-destroying phenotype.

*P. aeruginosa* strain MPAO1 was selected for the studies disclosed herein based on our work tracking dynamic virulence expression in *P. aeruginosa* in response to environmental stimuli and host tissue factors. At baseline, MPAO1 is a low virulence expressing strain that in general requires exposure to local environmental cues and host tissue factors to cause severe injury such as lethality in worms (*C. elegans*) and gut-derived sepsis mice. As *P. aeruginosa* is one of the most common pathogens to colonize the gut following radiation, anastomotic leak was modeled with a microbial strain that is well-characterized, of low virulence potential at baseline, and with a publically available transposon library.

The discovery of the involvement of mexT in the P1 to P2 transition is intriguing. MexT has been described as a mutational "hot spot" in *P. aeruginosa* [16,32]. MexT belongs to a LysR-type transcriptional regulator whose expression determines the global transcription profile, including the MexEF-OprN efflux pump, quorum-sensing system, and type III secretion system. Strains of *P. aeruginosa* with functional MexT display nfxC-type antibiotic resistance that is characterized by increased resistance to chloramphenicol and fluoroquinolones, and the same profile was observed in the MPAO1 strain (P1). Among other phenotypic characteristics of nfxC-type resistant *P. aeruginosa* strains is abolished swarming motility and attenuated pyocyanin, elastase, and rhamnolipids production. Strain MPAO1 (P1 phenotype) displayed characteristics similar to that described for nfxC-type strains, however its pyocyanin production, although indeed delayed in liquid media, was enhanced on agarized media. Overall, nfxC-type strains are considered to display attenuated virulence. The known conversion between nfxC and non-nfxC strains is associated with the insertion of an 8 bp sequence (CGGCCAGC; SEQ ID NO:5) in the mexT gene. The sequence of the MPAO1 genome harbors the insertion of the 8 bp sequence in the mexT gene that determines its P1 phenotype, similar to that described by Kohler as the nfxc-type mutation [35]. The conversion of P1 to P2, however, was not accompanied by the deletion of the 8 bp insertion, but by the mutation C→A that reverted MexT back to the non-functional state, indicating that several mechanisms of transformation exist. That the exact same mutation (i.e., C→A) that reverted MexT back to the non-functional state emerged both in vivo (at the site of anastomosis) and ex vivo (co-incubation with anastomotic tissues) appears to indicate the presence of an inducing factor (s) originating from the host, the microbe, or their interaction. Paradoxically, the non-nfxC strain harboring the 8 bp insertion is considered to be wild-type (wt) and the nfxC-type strain with a functional MexT is considered to be mutant [35]. Given that it would seem incongruous that a gene would emerge whose functionality is initially blocked, we considered that strains with the 8 bp insertion to be the mutant, with the strain lacking this insertion identified as the wild-type strain. Without wishing to be bound by theory, strong selection for the SNP mutation at the site of the anastomosis as an adaptive response to local microenvironmental conditions present as a result of tissue injury and radiation, provides a mechanistic explanation of the switch from wt P1 to P2.

The possibility of spontaneous conversion of P1 to P2 was ruled out in the study described herein by subculturing both the P1 and P2 strains for 20 passages in rich nutrient TSB media. No P2 phenotype was detected in P1 populations and no P2 spontaneously reverted to P1 among 100 colonies selected for analysis at each point. Therefore, the P1 to P2 conversion in the cecum (5-10%) and its high rate of conversion at anastomotic sites (>90%) are both a function of the in vivo environment per se as well as the tissue injury, which obviously plays a more prominent role. It is important to keep in mind that the cecum of post-operative rats remains a stressed environment as the host has undergone general anesthesia and major intestinal surgery and metabolically is still in recovery phase. Therefore, local cues within the cecum, albeit less when compared to the anastomotic site, contribute to the induction or selection for the P2 phenotype as a result of the effects of systemic host stress.

Data from the present study support an evolving principle in microbial pathogenesis that the gut represents a unique niche in which there is a spatialized ecologic feedback that leads to emergent traits among its colonizing microbes. In the ever-changing chaos of this complex ecosystem, it is easy to imagine that a patient being prepared for intestinal cancer surgery with purgatives, antibiotics, radiation, and chemotherapy, who then undergoes a traumatic tissue injury while exposed to healthcare-associated pathogens, will harbor microbes whose virulence might be triggered by unique host and physico-chemical cues. The discovery of the P2 SNP confirms the importance of host factors as agents that play a key role in this response. Therapies that seek to target microbial virulence expression may have an ecological advantage over antibiotics that indiscriminately eliminate all potential pathogens and the protective microbiota with the real risk of the emergence of resistance. Host factors are expected to play a key role in microbial virulence expression leading to altered epithelial barriers and impaired anastomotic healing wherever anastomoses are found. Therapies that seek to target microbial virulence expression are expected to have an ecological advantage over antibiotics that indiscriminately eliminate all potential pathogens, and the protective microbiota, with the real risk of the emergence of resistance.

This disclosure provides data that facilitates unraveling the molecular details by which colonizing pathogens express enhanced virulence during surgical injury and contribute to anastomotic leak. More generally, the disclosure reveals mechanisms by which radiation and tissue injury increase susceptibility to infections.

Example 1

Materials and Methods
  Bacterial Strains.
  *Pseudomonas aeruginosa* strain MPAO1 obtained from the transposon mutant library at the University of Washington was used for initial inoculation in rats and is herein designated as the P1 strain. The transformed strain harvested from leaking rat anastomoses was designated a P2 strain as it is derived from the original MPAO1 strain (see results below). P1 and P2 strains were used in the comparative in vitro experiments. For each experiment, strains were directly cultured from a 10% glycerol stock stored at −80° C. onto tryptic soy broth (TSB) agarized plates, and incubated at 37° C.; cells growing overnight were used in all experiments according to the respective design.

Rat Model of Colorectal Anastomotic Leak.

All experiments were approved by the Institute for Animal Care and Use Committee at the University of Chicago. All studies involving mice conformed to the Animal Welfare Act and NIH Guidelines for the care and use of animals in biomedical research and with the University of Chicago Carlson Veterinary guidelines.

Adult, male Wistar rats 300-350 g (Charles River Laboratory) were used for all experiments. Animals were allowed unrestricted access to rat chow and tap water throughout the experiments. In order to mimic the clinical practice of surgery for rectal cancer, rats were subjected to pre-operative fractionated pelvic radiation followed by a low colorectal resection and anastomosis. Prior to irradiation rats were sedated (40-80 mg/kg ketamine, 5-10 mg/kg xylazine; intraperitoneal injection, IP), and then placed in the supine position beneath the radiation cone. A total of 25 Gy of radiation, fractionated over 5 consecutive days (5 Gy per day; 1.47 Gy per minute), was delivered to the sigmoid colon and rectum using a Phillips RT250 x-ray generator. All other abdominal organs were excluded from the radiation field using a lead shield. One week after the last day of irradiation, rats were subjected to a laparotomy using aseptic technique and a 0.5 cm segment of colon at the peritoneal reflection was resected and an end-to-end rectosigmoid anastomosis was performed using 13 interrupted 6-0 Prolene sutures. After anastomosis formation, integrity was confirmed in all cases using a 5 ml saline rectal enema. In order to mimic nosocomial bowel contamination by *Pseudomonas aeruginosa*, an overnight culture of strain MPAO1 (200 µl of $10^7$ CFU in 10% glycerol) was directly injected into the cecum with a 25-gauge needle. The abdomen was closed in 2 layers using 4-0 Vicryl. Four groups of rats were studied: rats subjected to resection and anastomosis only (Group I), rats subjected to resection and anastomosis+cecal *P. aeruginosa* (Group II), rats subjected to preoperative radiation+resection and anastomosis (Group III), and rats subjected to preoperative radiation+resection and anastomosis+cecal *P. aeruginosa* (Group IV) (FIG. 1A). On postoperative day 6, all animals were euthanized and the anastomotic site evaluated for gross leakage using a 5 ml rectal methylene blue enema followed by excision of the cecum and anastomotic segment for microbial and histologic examination.

Prevention of *p. Aeruginosa*-Mediated Anastomotic Leak with Topical Phosphate+PEG (PEG/Pi).

5% PEG 15-20 dissolved in 25 mM potassium phosphate buffer, pH 6.0, was administered via rectal enema (5 ml) to the anastomotic suture site at the end of the surgery.

Histology.

For histological evaluation, a 5 mm×5 mm segment of tissue centered at the anastomotic suture line was removed and fixed in formalin overnight at 4° C. Each tissue segment was then embedded in paraffin with the suture line mounted vertically within the block, cut into 5 µm sections, and stained with hematoxylin and eosin. Light microscopy was performed using a Zeiss Axioskop and images where captured using a Zeiss Axiocam digital color camera (1.25× magnification).

Scanning Electron Microscopy (SEM).

To prepare for imaging with SEM, tissues were dissected into ice cold PBS, transferred to 4% paraformaldehyde Solution (USB 19943), and gradually dehydrated in 25% ethanol-PBS (i.e., EtOH-PBS), 50% EtOH-PBS, 75% EtOH-PBS, 90% EtOH-PBS, and 100% EtOH for 40 minutes per each step. The samples were then transferred to 50% EtOH-HMDS (Hexamethyldisilazane Ted Pella 18605) for 1 hr and then 100% HMDS for an additional hour. Next, samples were transferred to freshly prepared 100% HMDS and maintained overnight in the hood to ensure evaporation. Samples were then fixed to a carbon stubs (Ted Pella 16111-9, Specimen mounts, Aluminum, 9 mm high, Ted Pella Carbon tape 9 mm, 16084-3), sputter coated with 80% Pt/20% Pd to 12 nm with Cressington Sputter Coater 208HR, and viewed in Fei Nova Nano SEM200.

Wound Healing Assay.

For wound healing experiments, IEC-18 cells (ATCC, Cat. No. CRL-1589) were seeded onto collagen-coated plastic p35 dishes and grown to confluent monolayers. Monolayers were scratched with a 10 µl pipette tip, incubated for 1 hour at 37° C., and the initial wound width was then measured. 200 µl of *P. aeruginosa* strains (MPAO1-P1 or MPAO1-P2, OD=0.5) were added to culture dishes followed by incubation for 24 hours at 37° C., and the wound width was then re-measured. For experiments involving PEG/Pi treatment, cell medium was removed from wounded cells after 1 hour of incubation and replaced with 2 ml of 5% PEG dissolved in DMEM media supplemented with 25 mM phosphate buffer, pH 6.0) and incubated for 1 hour at 37° C., after which media was replaced with antibiotic-free DMEM media followed by bacterial inoculation as described. The values were expressed as the percentage of the initial wound healed.

LDH Release.

To quantitatively measure cell lysis, the amount of lactate dehydrogenase (LDH) released from the cells was measured after 24 hours using CytoTox 96 Cytotoxicity Assay (Promega, Madison, Wis.).

*Caenorhabditis elegans* Killing Assay.

The *C. elegans* assay was performed as previously described [10,11] with slight modifications to include a shorter pre-fasting procedure that made *C. elegans* less susceptible to infection. Briefly, synchronized L4-young adult nematodes were transferred from *E. coli* OP50 stock plates onto plain agarized plates, followed by a second transferring onto new plain agarized plates (60 mm diameter, Falcon). Next, 1 ml of 100 µg/ml kanamycin was poured on the agar surface, and after 3 hrs worms were re-transferred to experimental *P. aeruginosa* lawns (MPAOP1 or MPAO1-P2) grown on NGM low phosphate agarized media (agar 17 g/L (Fisher), peptone 2.5 g/L (Sigma), cholesterol 5 mg/L (Sigma), NaCl 3 g/L, $MgSO_4$ 1 mM, $CaCl_2$ 1 mM, ampicillin, 40 µg/ml). Plates with *P. aeruginosa* were incubated overnight at 37° C., adjusted to room temperature for 1 hr, seeded with 5 pre-starved worms in 5 replicates per experiment performed, and incubated at 23° C. Mortality of worms was then followed dynamically for 60 hr.

Random Amplified Polymorphic DNA Fingerprint Analysis.

To verify that the *P. aeruginosa* strain recovered from the tissue of our experimental animals was of a similar genetic background as the stock lab strain MPAO1, random amplified polymorphic DNA (RAPD) PCR fingerprinting was used as previously described [12]. DNA was isolated from the stock PAO1 strain and *P. aeruginosa* strain recovered from the anastomoses of experimental animals using an Easy-DNA Kit (Invitrogen, Carlsbad, Calif.). Primers 208 (5'-ACGGCCGACC-3'; SEQ ID NO:6) and 272 (5'-

AGCGGGCCAA-3'; SEQ ID NO:7), nucleotides producing reproducible polymorphisms with *P. aeruginosa*, were used for PCR.

Collagenase Assay.

Collagenase activity was assessed using an EnzChek Gelatinase/Collagenase Assay Kit (Molecular Probes, Eugene, Oreg.). *P. aeruginosa* strains were grown overnight in liquid TSB media and then diluted 1:100. For the assay, 180 µl of diluted bacteria in liquid TSB was added to 20 µl of collagen substrate (100 µg/ml; DQ collagen, type I from bovine skin, fluorescein conjugate; DQ collagen, type IV from human placenta, fluorescein conjugate). The negative control consisted of 180 µl TSB only added to 20 µl of collagen substrate. The reaction was measured every hour for 5 hours at an absorbance of 495 nm with a fluorescence microplate reader (FL ×800, Bio-Tek Instruments Inc), where the increase in fluorescence measured is proportional to proteolytic activity. Values obtained for negative controls were subtracted from experimental samples to account for background fluorescence. All experiments were carried out in quintuplicate. At each time point, the OD of each sample was measured (at 600 nm) in order to normalize to the amount of bacteria in each sample.

Apoptosis/Necrosis Assay.

Rat intestinal epithelial IEC-18 cell were grown to a full confluence on Glass Bottom Culture Dishes (MatTek) in Dulbecco modified essential medium (DMEM) supplemented with 5% fetal bovine serum, 1% penicillin/streptomycin (Gibco), and 0.01 U/ml insulin. Then medium was replaced by antibiotic-free/FBS-free DMEM medium, and IEC-18 monolayers were infected with either P1 or P2 to reach final concentration of $1 \times 10^6$ cfu/ml. Cell were incubated for 3 hrs at 37 C°, 5% $CO_2$, followed by analysis for apoptosis and necrosis using Apoptic&Necrotic&Healthy Cells Quantification kit (Biotium, Inc.). Images were obtained with Axiovert 35 (Zeiss, Germany) fluorescent microscope. Semi-quantitative analysis was performed by counting apoptotic and necrotic cells, and the counts were normalized to the number of nuclei stained by DAPI. Four fields of about 100 cells imaged from 4 independent dishes/group were included in the quantitative analysis.

Tight Junction Assay.

IEC-18 monolayers were prepared and infected as described above. After 3 hrs of co-incubation with P1 or P2, IEC-18 were washed twice with sterile PBS and fixed in 4% paraformaldehyde for 20 min at room temperature followed by PBS washes 3 times. Non-specific binding was blocked with blocking solution (1% BSA, 0.1% Triton X-100 in PBS) for 30 min. Tight junctions were labeled with rabbit anti-ZO-1 antibodies (1:250) (Invitrogen) overnight at 4° C. Cells were washed three times with PBS and incubated for 1 h at RT with secondary anti-rabbit antibodies conjugated to Alexa Fluor 488 (1:500) followed by PBS washes. Cells were visualized using a Leica DMIRE2 fluorescence microscope, SP2 laser scanning confocal (Leica microsystem, Mannheim, Germany).

Swarming Motility.

Medium for swarming motility assay consisted of 20 mM $NH_4Cl$, 12 mM $Na_2PO_4$, 22 mM $KH_2PO_4$, 8.6 mM NaCl, 1 mM $MgSO_4$, 1 mM $CaCl_2$, 11 mM dextrose, 0.5% casamino acids, 0.5% Bacto-agar (Difco) as previously described [13]. Plates were allowed to dry overnight at room temperature and then bacterial strains were inoculated from overnight grown PIA plates onto the swarming plates using a sterile toothpick followed by incubation at 30° C.

Pyocyanin Production.

In liquid media, pyocyanin was extracted into chloroform followed by re-extraction into 0.2N HCl, in which it was quantitated by the absorbance at 520 nm normalized to bacterial cell density, similar to previous descriptions [10, 14]. In agarized media, equal square pieces of agarized media with lawns (diameter 2 cm) were extracted from plates, bacterial cells were removed in 1 ml of 0.9% NaCl, and pyocyanin was extracted from homogenized agar by chloroform, followed by re-extraction into 0.2N HCl and measuring at 520 nm. Measurements were normalized to cell density measured by absorbance at 600 nm in 0.9% NaCl solutions.

Transformation of MPAO1 to the MPAO1-P2 Phenotype in Ex Vivo Experiments.

Laparotomy and low colorectal anastomosis formation were performed in animals that were either exposed or not exposed to preoperative pelvic radiation as described above. On postoperative day 1, all animals were sacrificed and the anastomotic segment and cecum (1 cm segment) were removed. Tissue segments (cecum, colon anastomosis) were homogenized in 1 ml sterile saline, incubated with strain MPAO1, and grown under static conditions, at 37° C. On day 3 of incubation, aliquots were plated onto *Pseudomonas* isolation agar (PIA) and 100 individual colonies were sub-cultured and evaluated for swarming motility. In selected experiments, tissue segments were homogenized in 1 ml of 5% PEG/Pi.

Genome Sequencing.

Genomic DNA sequencing was performed on both MPA01-P1 and MPA01-P2 using the Illumina GAIIx sequencer to a total of 137- and 115-fold coverage, respectively. Three libraries were created for each strain: 1×36 bp (370/340 million bp), 2×100 bp PE mate pairs with a 300 bp insert (320/180 Mbp) and 2×100 bp PE mate pairs with a 3000 bp insert (380/420 Mbp). All libraries were quality-controlled and assembled de-novo using the mira assembler [15]. The MPA01-P1 and MPA01-P2 assemblies contained 6.26 Mbp and 6.29 Mbp, in 125 and 363 contigs respectively. These MPA01-P1 and MPA01-P2 assemblies had 99.99 and 99.95% nucleotide identity to the PAO1/DSM-1707 strain previously described [16]. The strain genomes were aligned to the reference strain NC_002516 [17] using BRESEQ 0.13 (Barrick, J. BRESEQ, software) and to each other to determine areas of difference. The sequences are deposited in SRA as accession number SRA049017. These Whole Genome Shotgun projects have been deposited at DDBJ/EMBL/GenBank under the accession numbers AHKM00000000 and AHKN00000000. The version described in this report is the first version, i.e., AHKM01000000 and AHKN01000000.

Replacement of mexT in the P2 Strain.

The lambda Red-based technique modified for *P. aeruginosa* [18] was used for replacement of mexT in the P2 strain. The entire coding region of mexT from MPA01 was amplified using primers forward 5' CGG ATA ATG ATC GGG GGT AT 3' (SEQ ID NO:8) and reversed 5' CCG AAT TTT TCC AGC TCC TC 3' (SEQ ID NO:9), and 10 µl of amplified mexT-P1 was directly transformed in MAPO1-P2/pUCP18-RedS electrocompetent cells. Transformants were selected by plating on PIA containing 300 µg/ml of chloramphenicol. A cure of the plasmid was achieved on plates containing 10% sucrose. Transformants were verified for correct PCR insertion by mexT sequencing using primers Forward 5' GCC TGT CAG TGA TCC TAT GC 3' (SEQ ID NO:10) and Reversed 5' GAT CGC CGA TGA ACA TGC 3' (SEQ ID NO:11).

Statistical Analysis.

Statistical analysis of anastomotic leak rate was performed using Fisher's Exact Test (Prism software). Significance for ex vivo studies was determined using 1-way ANOVA analysis. All other non-parametric data were analyzed using Kruskal Wallis and Mann-Whitney tests. Kaplan-Maier survival graph was analyzed using SPSS software. Significance was determined as a p-value <0.05.

Example 2

Figure 8:
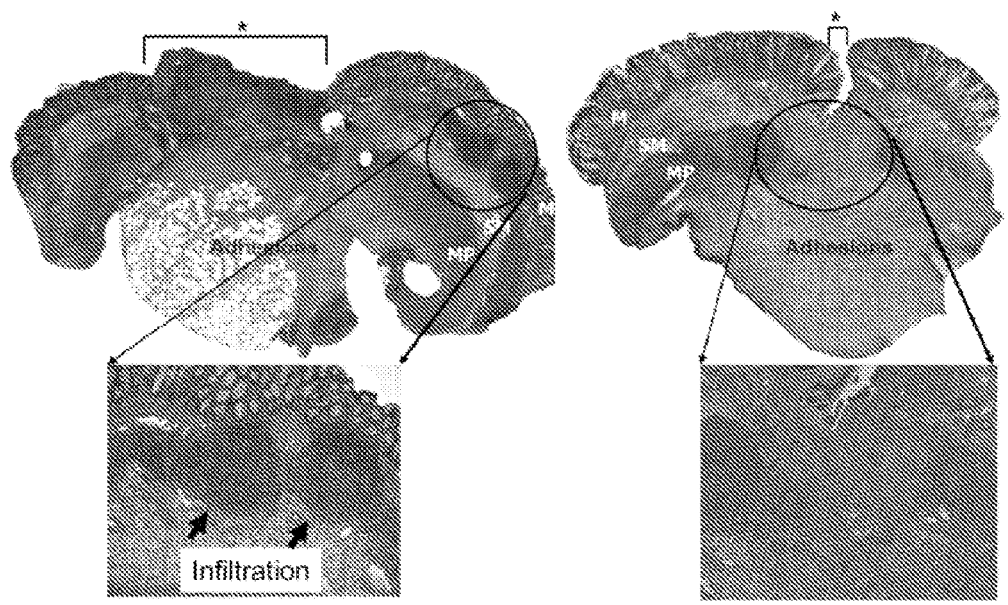
FIG. 8. Histology of anastomoses. Histological analysis of anastomotic tissues from rats of experimental groups II and IV. M=mucosa; SM=submucosa; MP=muscularis propria; *=anastomosis.

Intestinal Exposure to Radiation and *P. aeruginosa* Causes Spontaneous Anastomotic Leak in Rats In order to define the role of *P. aeruginosa* on anastomosis healing, we first developed a novel anastomosis model in which rats were subjected to preoperative fractioned radiation similar to clinical practice. Rats then underwent distal colon resection and anastomosis followed by intestinal inoculation with *P. aeruginosa* via cecal puncture at the end of the operation (Group IV) (FIG. 1A). Control groups included: rats subjected to resection and anastomosis only (Group I), rats subjected to resection and anastomosis+cecal *P. aeruginosa* (Group II), rats subjected to preoperative radiation+resection and anastomosis (Group III). When the anastomoses of all rats were tested and directly examined on postoperative day (POD) six, rats in group IV demonstrated evidence of a significant incidence of spontaneous anastomotic leak with grossly visible disruption of the anastomotic suture line (FIG. 1B), dense adhesions to the anastomosis, immune cell infiltration (FIG. 1C, FIG. 8), and gross extravasation of injected intraluminal (rectal) contrast material (methylene blue) (FIG. 1D').

Figure 2:
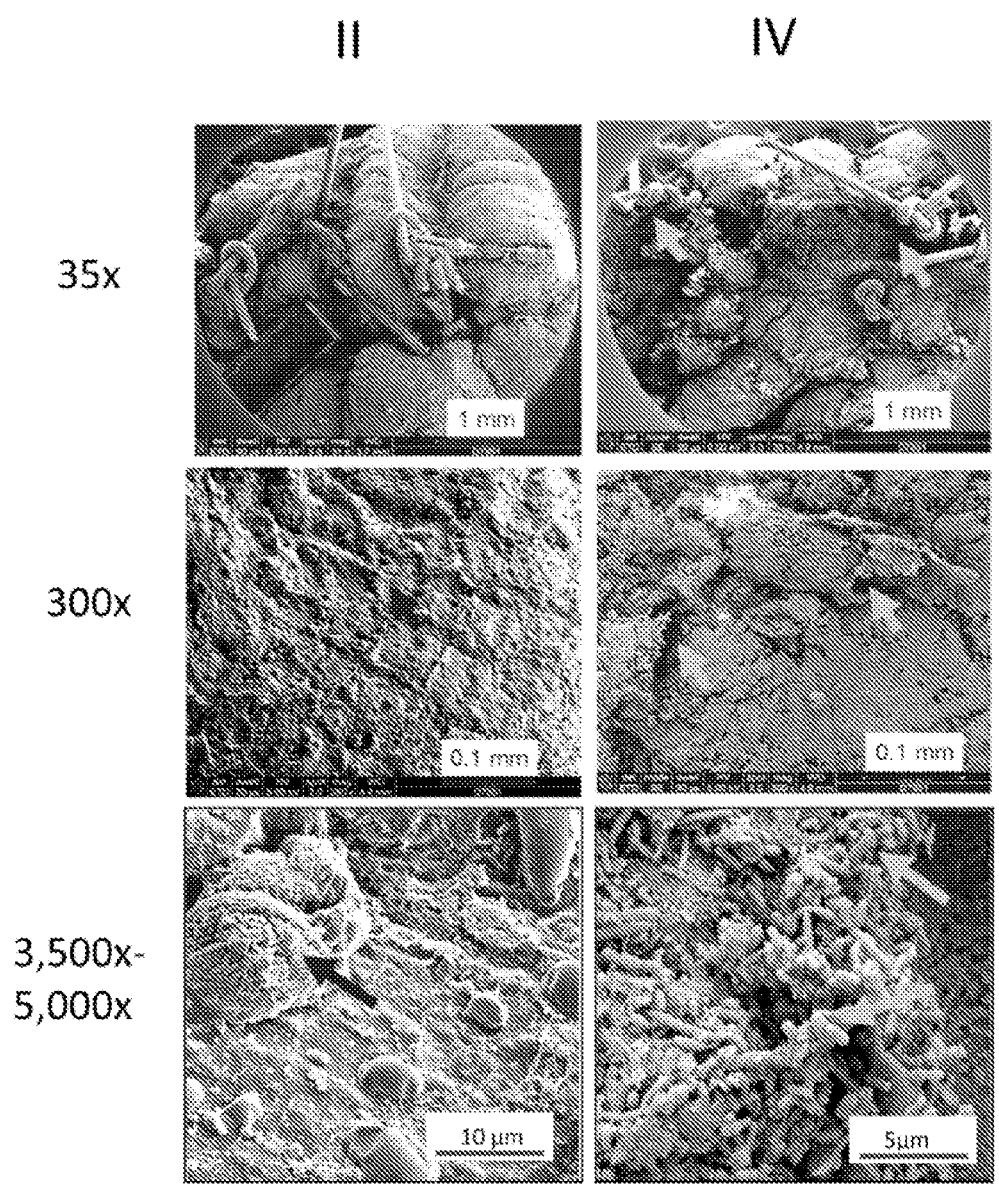
FIG. 2. Scanning electron microscopy (SEM) images of anastomosis tissues. Blue arrows indicate healed anastomosis (30×), intact intestinal epithelium (300×), and macrophages on epithelial surface (3,500×) in group II. Orange arrows indicate discontinuity near or at the anastomosis (30×), disrupted intestinal epithelium (300×), and a high degree of bacterial colonization/adherence at the edge of non-healed anastomoses (5,000×). 50 images from each group of 5 mice were obtained, and representative images are displayed.

A major distinguishing characteristic in well-healing and intact anastomoses appeared to be the absence of dense adhesions to the external aspects of the anastomotic suture line, grossly intact and visible anastomotic healing both externally and internally, and lack of extravasation when intraluminal contrast was injected. Gross histology confirmed these findings. When we opened the anastomoses and visualized the mucosa, anastomotic suture lines were intact in healed anastomosis but demonstrated focal disruptions in those that leaked. Scanning electron microscopy (SEM) of the mucosal of anastomotic suture lines in rats exposed to *P. aeruginosa* (groups II and IV) (FIG. 2) demonstrated in group II: an intact suture line at the anastomosis (35×), a smooth intact appearance of the epithelial surface (300×), and the presence of immune cells (macrophages) and few if any bacteria (3500×); in group IV: the suture line appears disrupted (35×), there is disintegration of the epithelial surface (300×), and there are abundant microbial cells at sites of disruption (3500×). Taken together, these findings demonstrate that when *P. aeruginosa* is introduced to the proximal colon of rats subjected to preoperative radiation and a distal colon anastomosis, the microbe adheres to anastomotic sites and causes leakage.

Example 3

Figure 3:
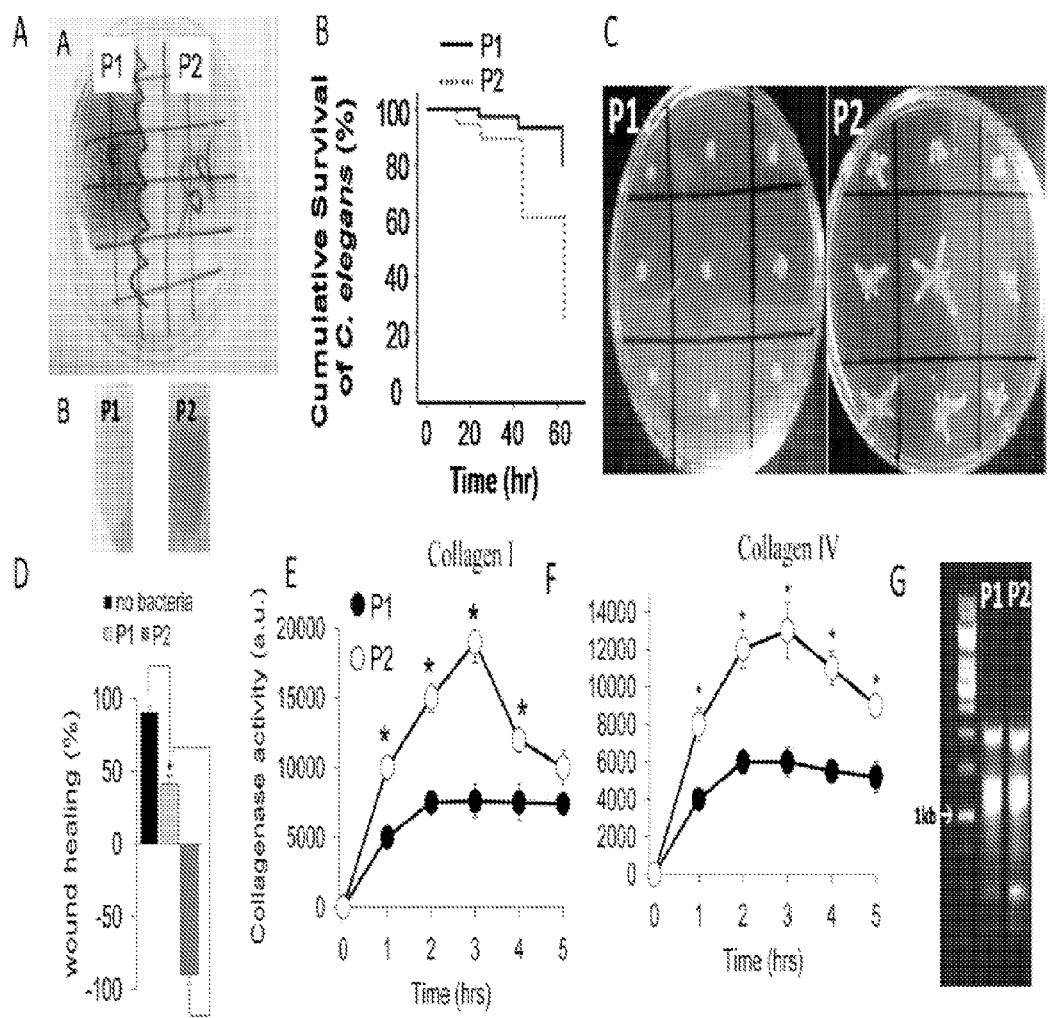
FIG. 3. P1 and P2 phenotypes of *P. aeruginosa* MPAO1. (A) Pyocyanin production seen as green color pigmentation on solid *Pseudomonas* isolation agar (PIA) and liquid TSB media. (B) Kaplan-Meyer survival curves of *C. elegans* N2 feeding on P1 and P2. Cumulative survival is represented of 2 experiments, n=7/dish, 5 dishes/experiment, p<0.01. (C) Swarming motility. (D) Wound healing assay. Wound width was calibrated and measured using the MicroSuite software for imaging applications (Olympus SZX16). Wound healing of −100% indicates a 2 fold increase in the wound width compared to the baseline width. n=12, *p<0.01. (E, F) Collagenase activity of P1 and P2 measured by degradation of fluorescent labeled collagen I (E) and collagen IV (F) as substrates. n=6, *p<0.01. Fluorescence values were normalized to cell density measured by absorbance at 600 nm. Results are representative of 3 independent experiments. (G) RAPD fingerprint analysis demonstrating a similar genetic background of the P1 and P2 phenotype strains.
Figure 4:
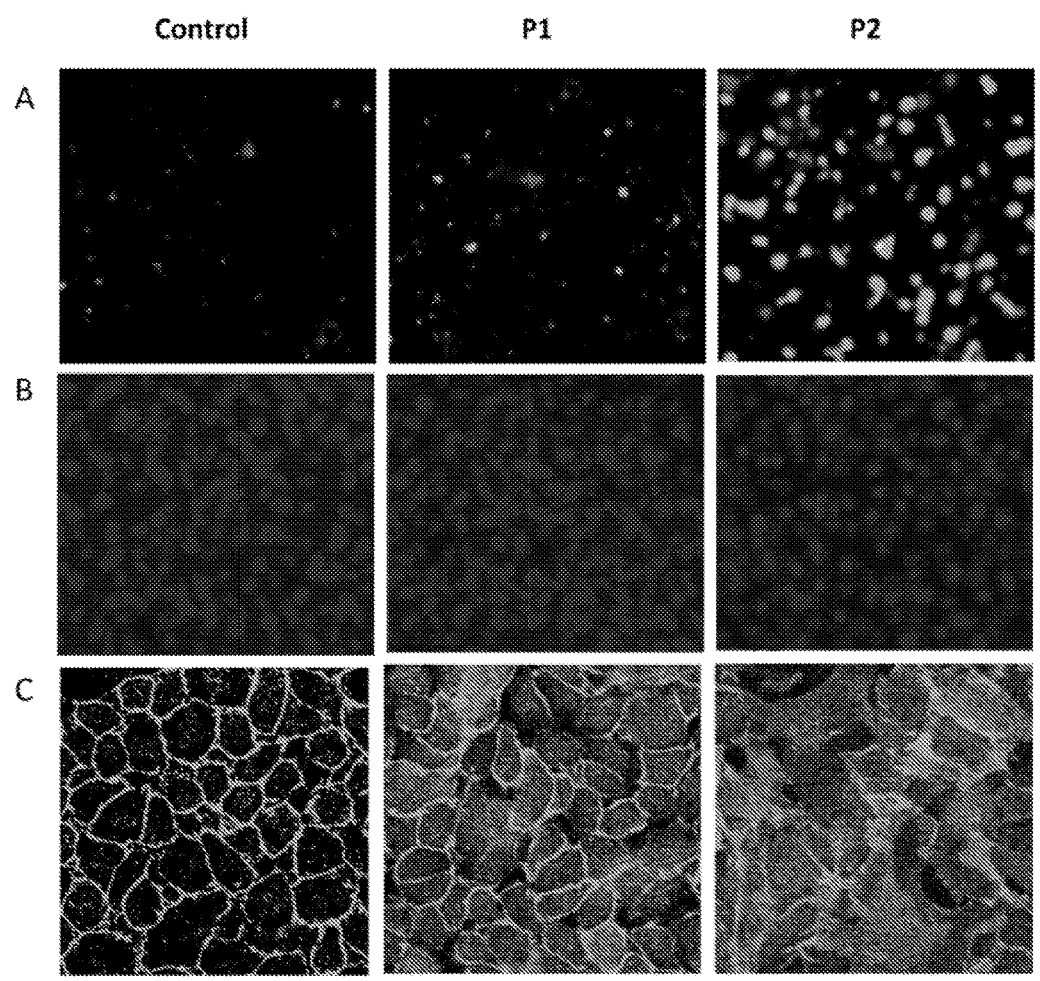
FIG. 4. P2 induces significant apoptosis and structural changes in the tight junction protein ZO-1 in IEC-18 monolayers. (A) IEC-18 cells infected with P1 and P2 for 3 hrs were analyzed for apoptosis and necrosis with Apoptic&Necrotic&Healthy Cells Quantification kit (Biotium, Inc.) using fluorescence microscope Axiovert 35 (Zeiss, Germany). FITC-Annexin V (apoptotic cells, green), EtD-III (necrotic cells, red). (B) Staining of nuclei with Hoechst 33342. (C) IEC-18 monolayers treated with antibody to ZO-1.
Figure 9:
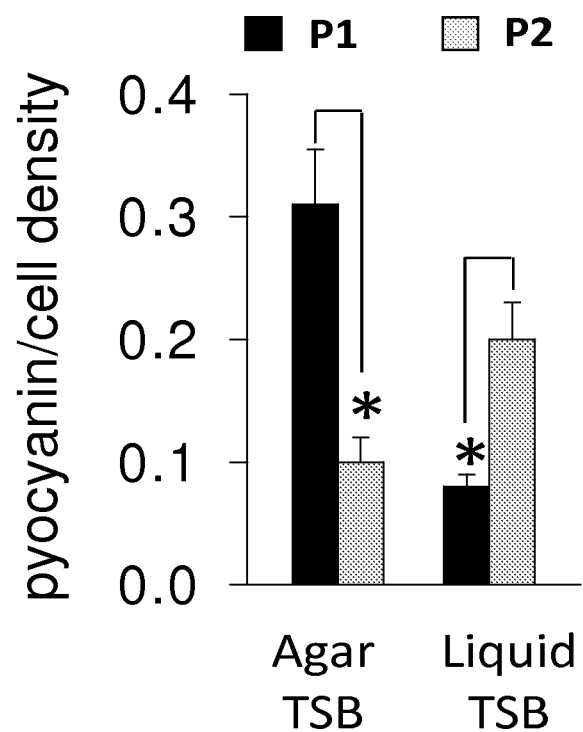
FIG. 9. Production of pyocyanin. Pyocyanin production in agarized and liquid media; TSB=tryptic soy broth; n=5/group; *p<0.01.
Figure 10:
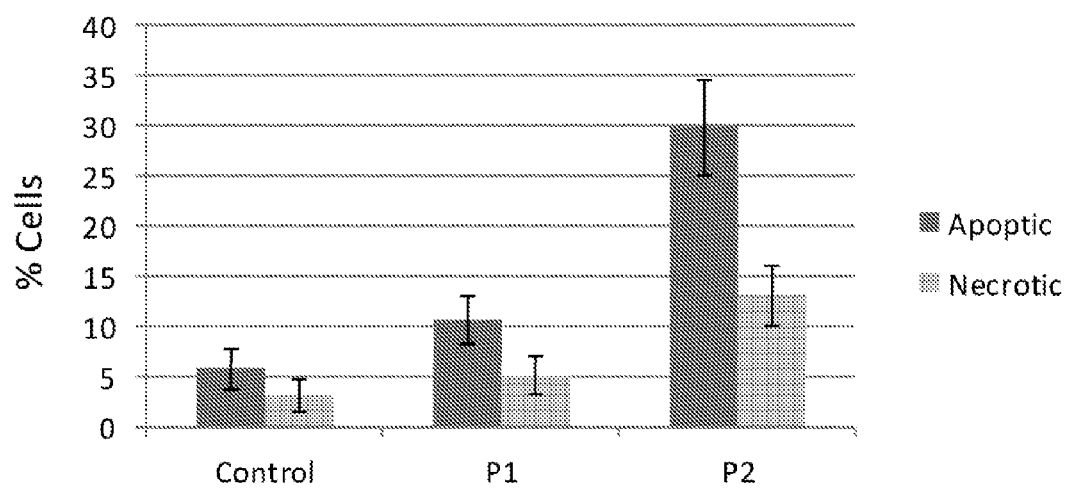
FIG. 10. Apoptosis and necrosis. The percentage of apoptotic and necrotic IEC-18 cells co-incubated with P. aeruginosa of the P1 and P2 phenotypes. The counts were normalized to the amount of nuclei stained by DAPI. Four fields of about 100 cells imaged from four independent dishes/group were included in the quantitative analysis.
Figure 11:
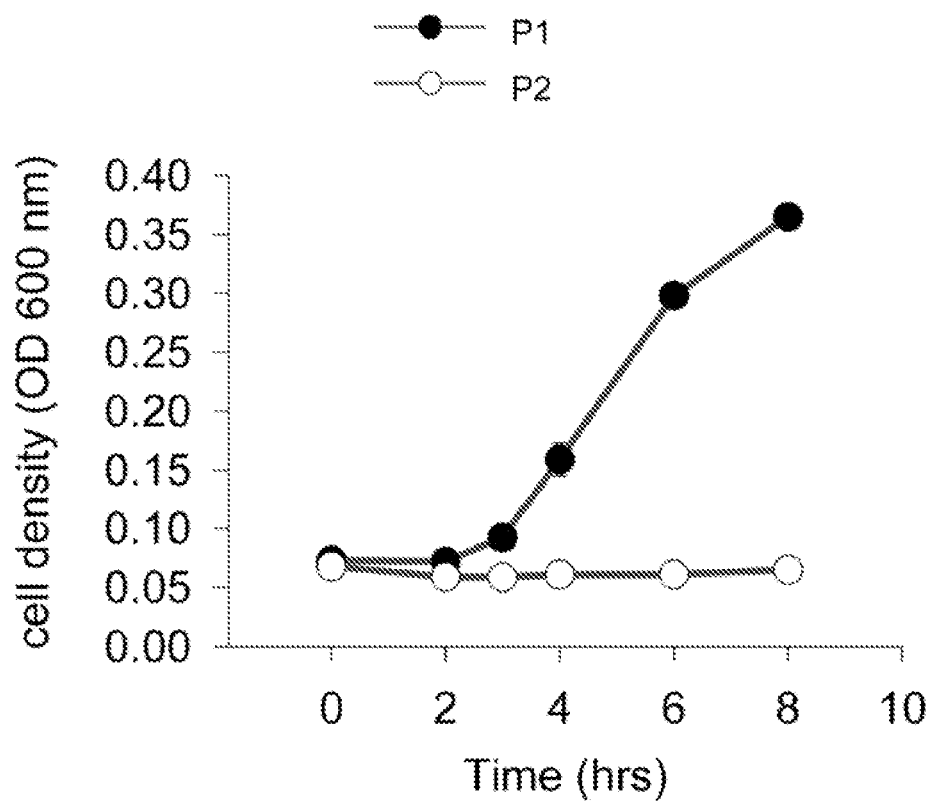
FIG. 11. Chloramphenicol resistance of P1 and P2 strains. Strains were cultured in TSB containing 250 μg/ml chloramphenicol and grown in 96-well plate (150 μl/well, shaking at 150 rpm, 37° C. Cell density was measured on Plate Reader at OD 600 nm. Values represent the mean of triplicate cultures.
Figure 13A:
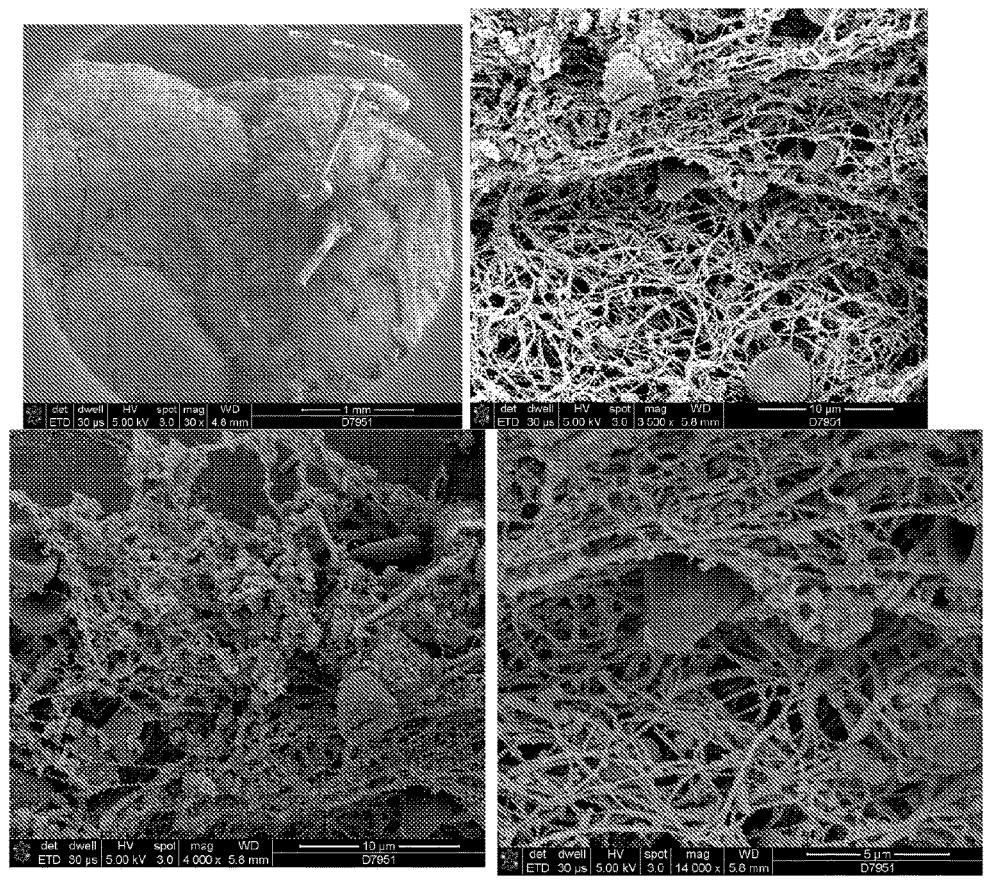
FIGS. 13A-13C. P-PEG nanonets. A close-up of P-PEG from the rat experiments described herein, demonstrating that P-PEG forms a synthetic nanonet, which is important in trapping bacteria and preventing them from causing epithelial cell layer invasion/damage.
Figure 13B:
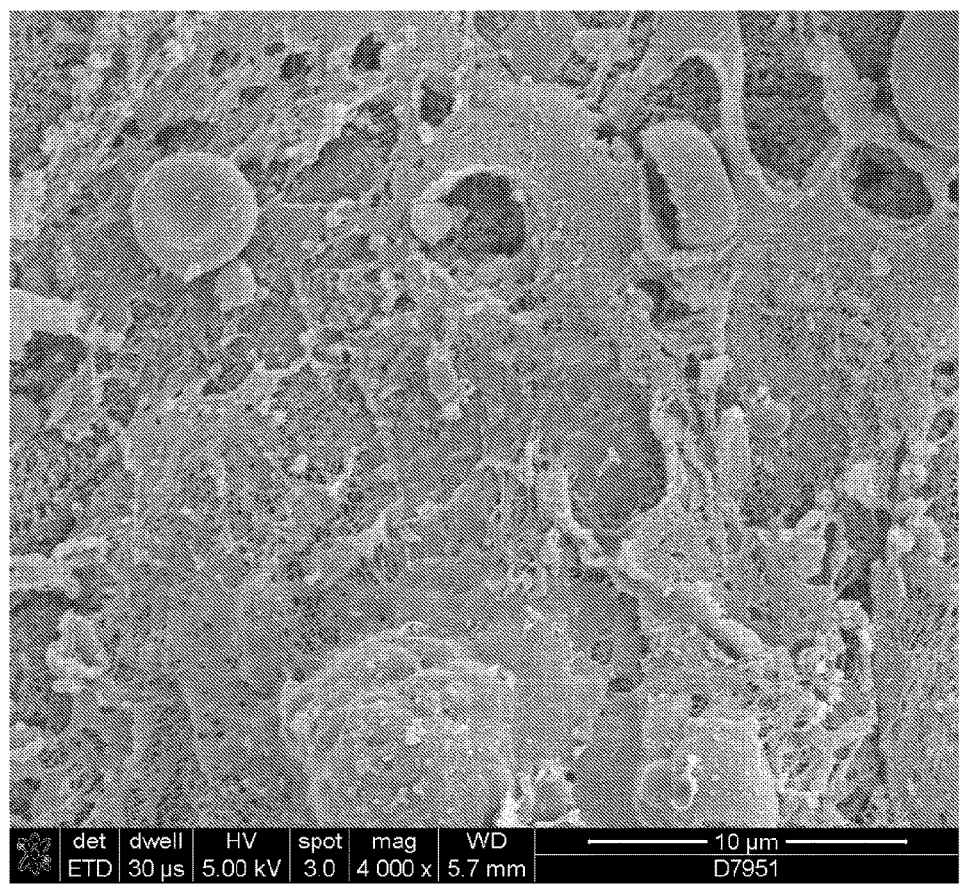
Figure 13C:
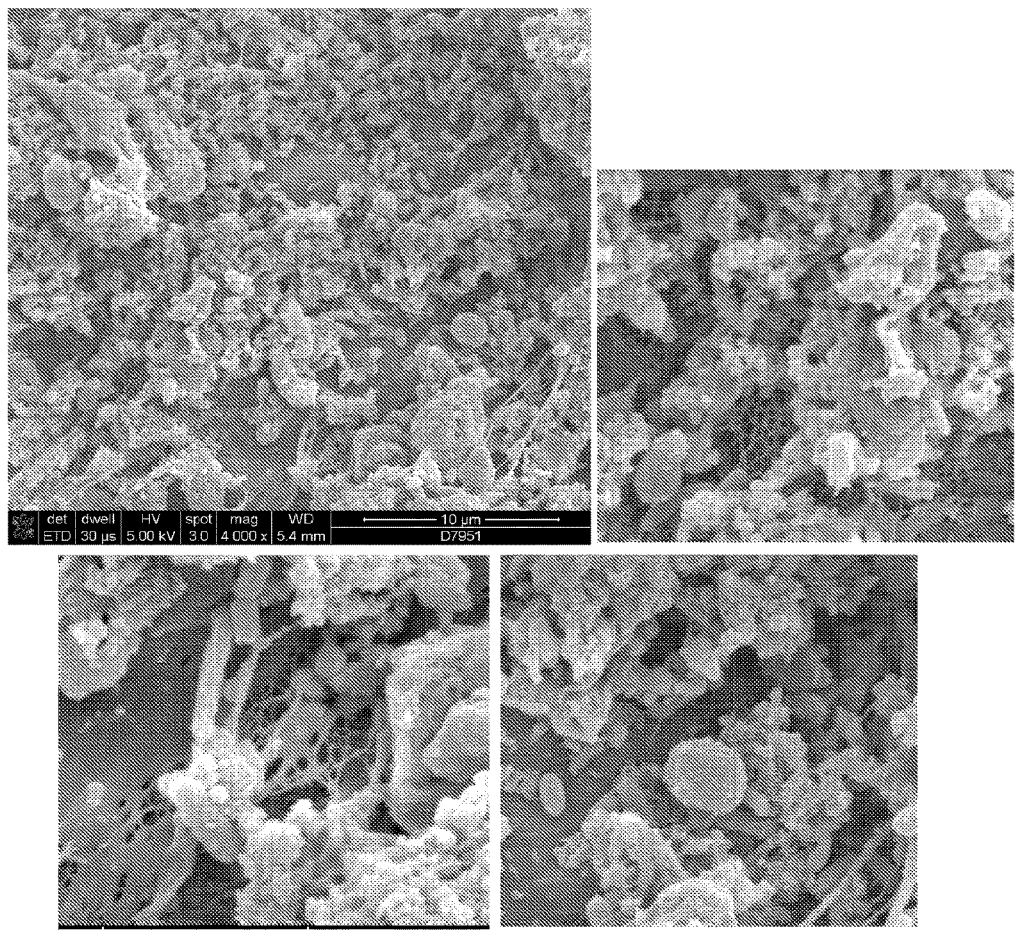

*P. aeruginosa* Isolated from a Disrupted Anastomosis Displays a Tissue-Destroying Phenotype An experiment was conducted to determine whether strains of *P. aeruginosa* isolated from a leaking anastomosis would display an enhanced virulence phenotype. In particular, the phenotype of *P. aeruginosa* recovered from leaking anastomotic sites in rats subjected to radiation exposure and intestinal inoculation with *P. aeruginosa* (group IV) were compared to the inoculating MPAO1 strain. On postoperative day 6 (POD 6) leaking disrupted anastomoses were resected, homogenized and *P. aeruginosa* was recovered by plating tissues on *Pseudomonas* isolation agar (PIA). Hundreds of single colonies were directly chosen from the plates and re-plated (streaked) on fresh PIA plates. We found that majority of colonies displayed low pyocyanin production which we initially recognized as displaying attenuated virulence (FIG. 3A, top panel). To confirm this, the virulence of these colonies in *C. elegans* was tested and the surprising results showed enhanced killing of the yellow colonies compared to the initial strain (FIG. 3B). Also observed were dendritic-like edges of lawns generated by the yellow colonies indicating that they possessed swarming motility. Therefore, swarming assays were performed. High swarming motility was observed in these cells, in contrast to almost no swarming activity in the initial strain (FIG. 3C). The strains were then tested for their ability to disrupt cellular elements of anastomotic tissues (epithelial cells, collagen) and both an enhanced epithelial cell destruction (FIG. 3D) and a high level of collagenase (FIG. 3E,F) were observed among the yellow-appearing colonies. To verify that the strain recovered from leaking anastomotic tissues was genetically similar to the wilt-type strain used for intestinal inoculation (MPAO1), and not a pre-existing commensal in the rat gut, genetic fingerprint analysis (RAPD) was performed, which confirmed their similarity (FIG. 3G). Surprisingly, virtually all colonies isolated from disrupted anastomoses were attenuated in the production of the toxic metabolite pyocyanin grown on PIA at high cell density. Conversely, when grown in liquid culture, there was an increase in pyocyanin production compared to MPAO1 (FIG. 3A bottom panel, and FIG. 9). Spontaneous conversion of P1 and P2 in vitro was tested by subculture to 20 passages of each in rich nutrient TSB media. No P2 phenotype was detected in subcultures of P1 and conversely no P1 was detected in subcultures of P2, and the pattern of pyocyanin production by P2 (low on PIA, high in liquid TSB) was stably reproduced. We named the isolate from disrupted anastomotic tissues MPAO1-P2 (herein termed P2) and the initial inoculating strain MPAO1-P1 (herein termed P1). The ability of P2 to degrade collagens demonstrates its ability to cause a full thickness defect at the site of anastomotic injury. Next the effect of P2 on apoptosis/necrosis and tight junctional integrity of cultured epithelial monolayers was assessed. Rat intestinal epithelial EIC-18 cells were infected with $10^6$ CFU P1 or P2 and incubated for 3 hrs followed by staining for apoptosis (FITC-Annexin V, green fluorescence), necrosis (EtD-III, red fluorescence), nuclei (Hoechst 33342, blue), and tight junction (ZO-1 immunostaining). Using confocal microscopy, we observed significant apoptotic cells in IEC-18 cells infected with P2 compared to P1 (FIG. 4A, and FIG. 10 demonstrating quantitative analysis of apoptotic cells). while nuclei staining demonstrated the same amount of the cells in both groups (FIG. 4B). About 10% of IEC-18 cells appear to be necrotic at 3 hrs when exposed to P2 infection confirming its cytotoxicity (FIG. 4A). P2 also caused a striking loss of tight junction integrity as judged by ZO1 staining (FIG. 4C). Taken together these results demonstrate that the P2 phenotype expresses a degree of virulence that is sufficient to disrupt healing anastomotic tissues from the most superficial elements (epithelia) to the submucosa and serosa (collagen).

Example 4

Regional Distribution of P1/P2 within the Rat Colon

To determine the relative distribution of P1 versus P2 in the two treatment groups in which *P. aeruginosa* was injected into the cecum (groups II, IV), we selectively cultured for *P. aeruginosa* from the cecum and anastomotic sites and then assessed retrieved strains for swarming. Results demonstrate that cecal *P. aeruginosa* from both groups displayed a low incidence of the P2 phenotype (<10% of total recovered colonies). In contrast, a high incidence (>80%) of the P2 phenotype was recovered (by culture) at anastomotic sites in both non-radiated (group II) and radiated (group IV) rats indicating that surgical injury plays a role in the transformation to, or selection for, P2.

Example 5

Transformation of P1 to P2 using Ex Vivo Intestinal Tissues.

Figure 5:
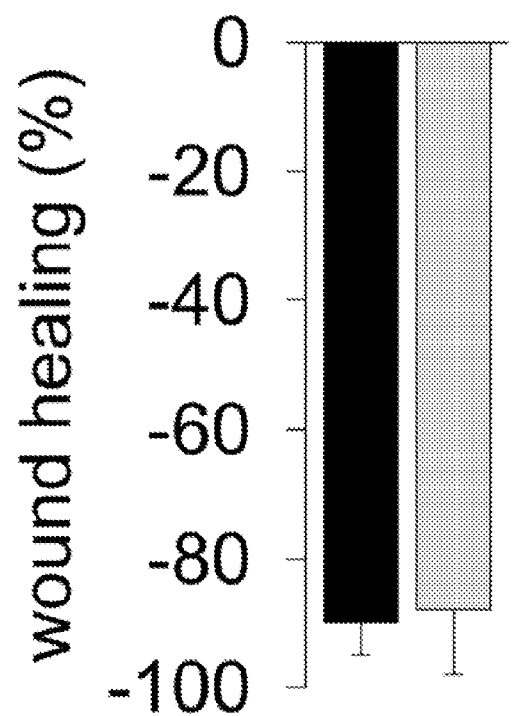
FIG. 5. Wound healing assay. The P2 strain recovered from anastomotic tissues (in vivo) and the P2 strain recovered after co-incubation of MPAO1 with anastomotic tissues (ex vivo) similarly destroy wounded epithelial IEC-18 monolayers.

To determine if anastomotic tissues themselves can shift P1 to P2, we performed experiments in which P1 was exposed to rat colon tissues ex vivo. Tissues were obtained from reiterative studies in rats subjected to a colon resection and anastomosis with no exposure to *P. aeruginosa* and rats without anastomosis. Cecum and colon segments were excised and homogenized in sterile saline. The P1 strain was added to the homogenate and the solution incubated at 37° C. After 72 hours, *P. aeruginosa* was recovered on PIA, and then examined for pyocyanin production and swarming motility. 80-90% of recovered colonies from anastomotic tissues were found to produce the P2 phenotype. No transformation was detected when P1 was incubated in saline alone and ~10% of colonies displayed the P2 phenotype when P1 was exposed to non-traumatized cecal tissues or non-anastomotic colon tissues. Comparative analyses of P2 transformed in vivo and P2 transformed ex vivo demonstrated similar ability to destroy wounded epithelial cell monolayers (FIG. 5). These findings suggested that factors present within colonic tissues themselves may be responsible for the shift of P1 to P2.

Example 6

SNP Mutation in mexT is Responsible for P2 Phenotype

Figure 6:
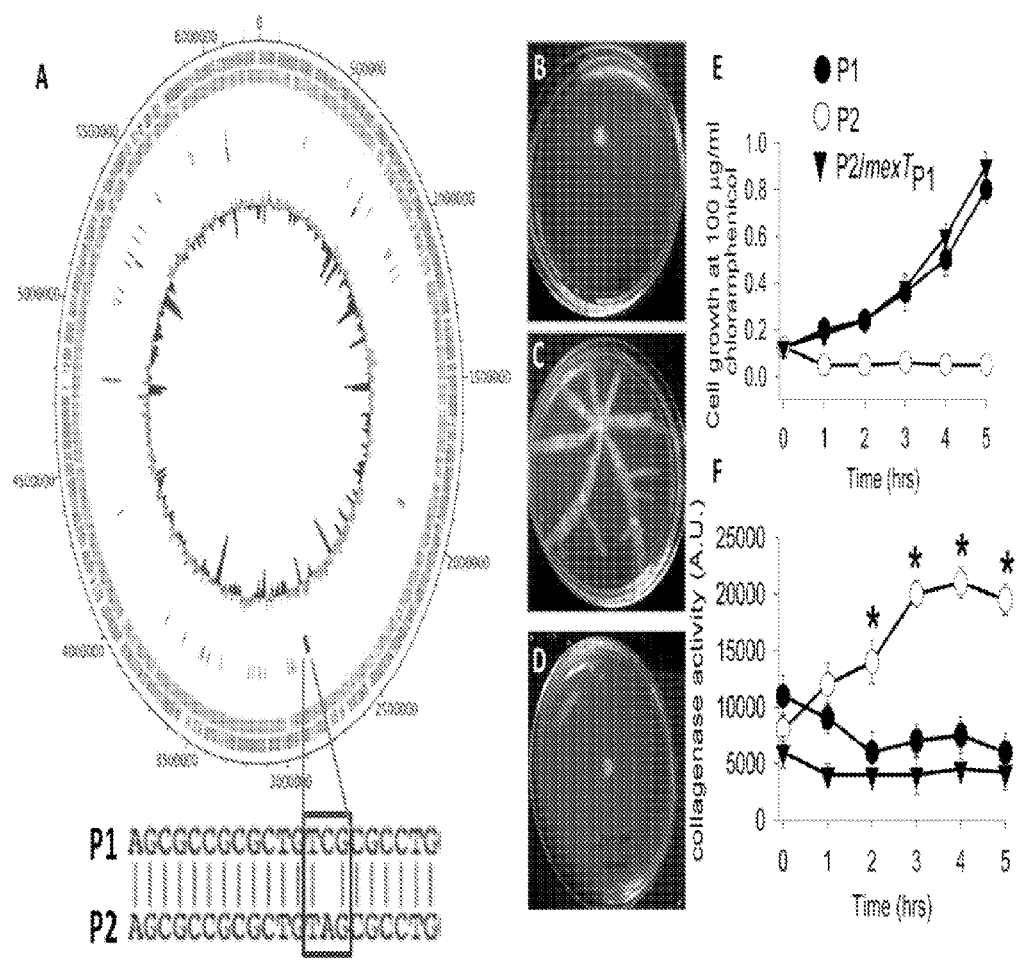
FIG. 6. SNP mutation in MexT is responsible for P2 phenotype. (A) Genome DNA sequence comparative map of *P. aeruginosa* MPAO1-P1 and MPAO1-P2 at the DSM-1707 backbone annotated with the MexT locus. Grey and teal bands: annotated coding regions; red tick: location of MexT locus; green ticks: tRNAs; black ticks: rRNAs; inner circle GC content. (B-D) swarming motility in (B) MPAO1-P1 (P1), (C) MPAO1-P2 (P2), and (D) MPAO1-P2 in which mexT was replaced by mexT gene amplified from MPAO1-P1 (P2/mexT$_{P1}$). (E) Growth curves at 100 μg/ml chloramphenicol demonstrating acquisition of chloramphenicol resistance in P2/mexT$_{P1}$. (F) Collagenase activity measured by fluorescence of fluorescent labeled gelatin as a substrate. n=6, *p<0.01. Results are representative of 3 independent experiments.

To determine if the observed shift from P1 to P2 was secondary to a genotypic change, genome sequencing was performed. A single nucleotide mutation (C→A position 2807731 in the NC002516 genome) localized in the mexT gene was identified (FIG. 6A). These results were further confirmed by direct sequencing of the amplified mexT in P1 and P2 strains using primers Forward 5' GCCTGTCAGT-GATCCTATGC 3' (SEQ ID NO: 12) and Reversed 5' GATCGCCGATGAACATGC 3' (SEQ ID NO: 13). Sequencing of amplified mexT from P2 strain isolated ex vivo demonstrated the same C→A SNP.

The mexT gene is predicted to encode a full-length, 304-residue MexT protein, a regulator of the MexE-MexF-OprN multidrug efflux system of *P. aeruginosa* [19]. The genome sequence demonstrated the intact mexT in P1 (Protein accession number Pubseed:fig|6666666.7915.peg.414) [20] while the SNP (C→A) mutation in P2 was found to create an in-frame stop codon, limiting the possible products to a 44-residue presumed non-functional truncated protein (Pubseed: fig|6666666.7916.peg.276), and a 242-residue product resulting from re-initiation of translation at M63 (Protein accession number Pubseed: fig|6666666.7916.peg.277) (GenBank Protein accession number for the intact MexT protein from PAO1 is AJ007825.1). The functionality of MexT can be assessed by the level of resistance to chloramphenicol and fluoroquinolones antibiotics that depends on MexT-regulated expression of genes encoding the multi-drug efflux pump MexEF-OprN [21, 22]. We assessed antibiotic resistance of P1 and P2 and observed that the P2 strain showed a 10-fold higher sensitivity to norfloxacin compared to the P1 strain (MIC 0.38 µg/ml for P1 and 3.8 for P2) and about 6 fold higher sensitivity to chloramphenicol (FIG. 9). To verify the SNP mutation on the phenotype shift, we replaced mexT-P2 by mexT-P1 in strain P2 to create P2/mexT$_{P1}$. This replacement led to the reversion of P2 to P1 phenotype as determined by the pyocyanin production pattern (high pyocyanin on agarized TSB, low pyocyanin in liquid TSB), absence of swarming (FIG. 6B-D), high resistance to chloramphenicol (FIG. 6E), and attenuated collagenase activity (FIG. 6F). Taken together, these data establish that the SNP mutation in mexT is responsible for transformation of the P1 to the P2 strain.

Example 7

Figure 7:
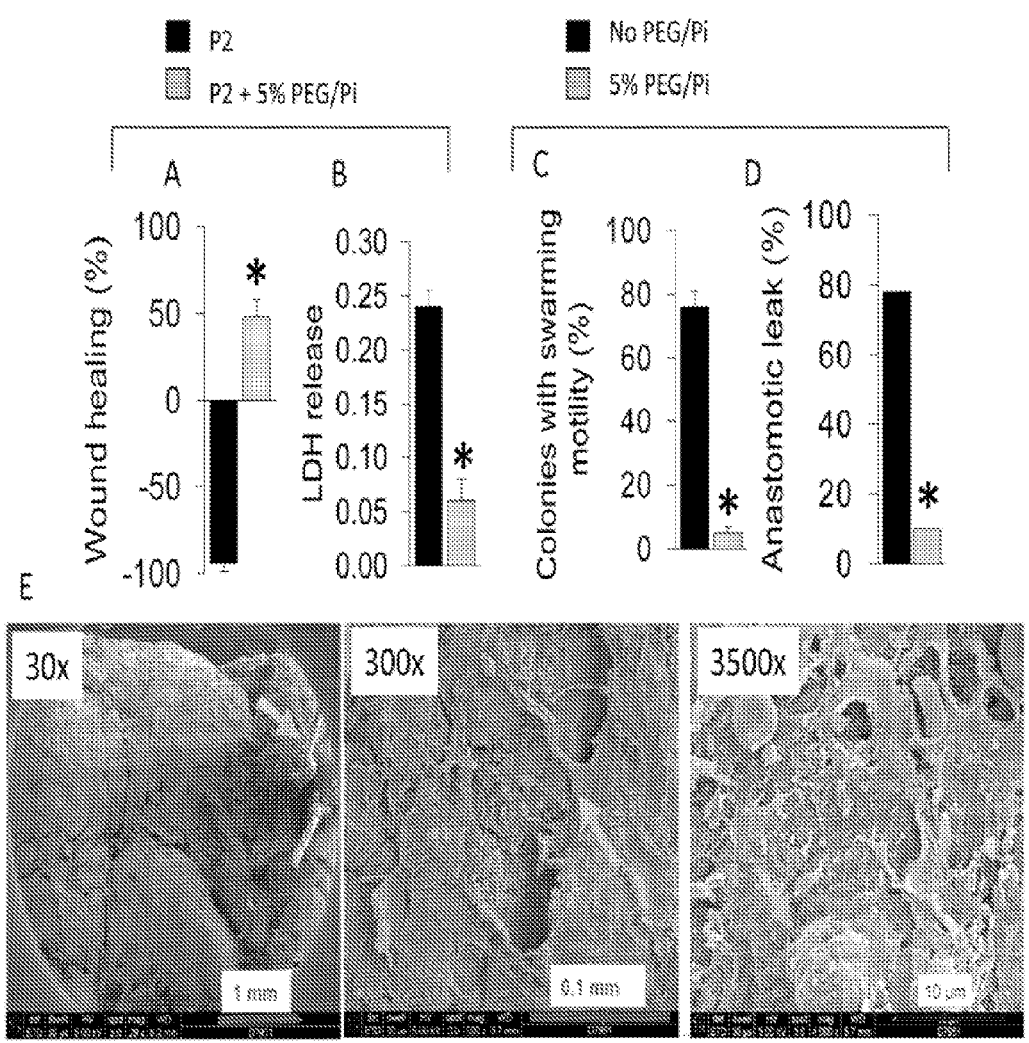
FIG. 7. Protective effect of PEG/Pi. (A) Inhibition of wound apposition (healing) by P. aeruginosa MPAO1-P2. n=5, *p<0.01. (B) Prevention of the cytotoxic effect of MPAO1-P2. n=6, *p<0.01. (C) Frequency of transformation MPAO1 to P2 phenotype. n=3, *p<0.01. (D) Frequency of anastomotic leak in rats. n=10, *p<0.01. (E) SEM images of anastomotic tissues treated with 5% PEG/Pi demonstrating intact intestinal epithelium covered with a mucus-like film structure.

Prevention of the P1→P2 Transformation is Associated with Complete Anastomotic Healing High molecular weight polyethylene glycol, e.g., PEG 15-20, attenuates virulence activation in *P. aeruginosa* in response to radiated epithelial cells and protects against post-radiated lethal sepsis. Phosphate was shown to be important to the prevention of virulence activation and lethality in *P. aeruginosa* via its effect on phosphosensory and phosphoregulatory pathways that connect to quorum sensing [10], an effect that is maximized at a pH of 6.0 [11]. Therefore a 5% PEG15-20 solution in 25 mM potassium phosphate buffer at pH 6.0 (herein named PEG/Pi) was tested in reiterative experiments. IEC-18 cells were pretreated for 1 hour with 5% PEG/Pi prior to P2 inoculation. A marked protective effect against P2-induced cytotoxicity/disruption was observed. Epithelial monolayers remained intact as judged by LDH released and demonstrated cellular migration across the wound to 50% (FIG. 7A,B). 5% PEG/Pi also prevented the transformation of P1 to P2 during exposure to anastomotic tissues ex vivo (FIG. 7C). Finally, reiterative studies in rats exposed to pre-operative radiation followed by colon resection, anastomosis, and cecal injection with *P. aeruginosa* P1 (group IV rats) with 5% PEG/Pi given as an enema demonstrated significantly attenuated anastomotic leak rates compared to rats given rectal saline (FIG. 7D). The causality between the transformed P2 phenotype in vivo and anastomotic leak in this model is indicated by the observation that no P2 strains were recovered from anastomotic tissues of rats treated with the PEG/Pi despite the compound having no microbicidal activity. This result was confirmed by the SEM analysis of anastomotic tissues treated with 5% PEG/Pi that demonstrated absence of bacteria on the epithelial surface and healed epithelial surfaces (FIG. 7E). Taken together, these results indicate that in vivo transformation of P1 to P2 plays a key role in anastomotic leak in this model and is prevented by virulence-directed agents such as PEG/Pi.

Example 8

PEG/Pi Prevents Anastomotic Leak in Rats with Ischemia

The promising results disclosed in Example 7 led to experiments designed to assess the effect of the PEG/Pi therapeutic on anastomotic leak in vivo. Rats were subjected to a distal colon resection and anastomosis. At time of surgery, the mesentery is ligated adjacent to the anastomosis to create ischemia (devascularization).

Three groups of animals were studied. Conventional techniques well known in the art were employed unless otherwise indicated. Group 1 underwent anastomosis only. Group 2 underwent anastomosis and ischemia, and was administered PEG/Pi. Group 3 underwent anastomosis and ischemia, and was not administered PEG/Pi. Group 2 received 5% PEG in 25 mM phosphate, which was administered via enema on postoperative day 0. Rats were sacrificed on postoperative day 6 to assess the amount of anastomotic healing or leakage.

Figure 14:
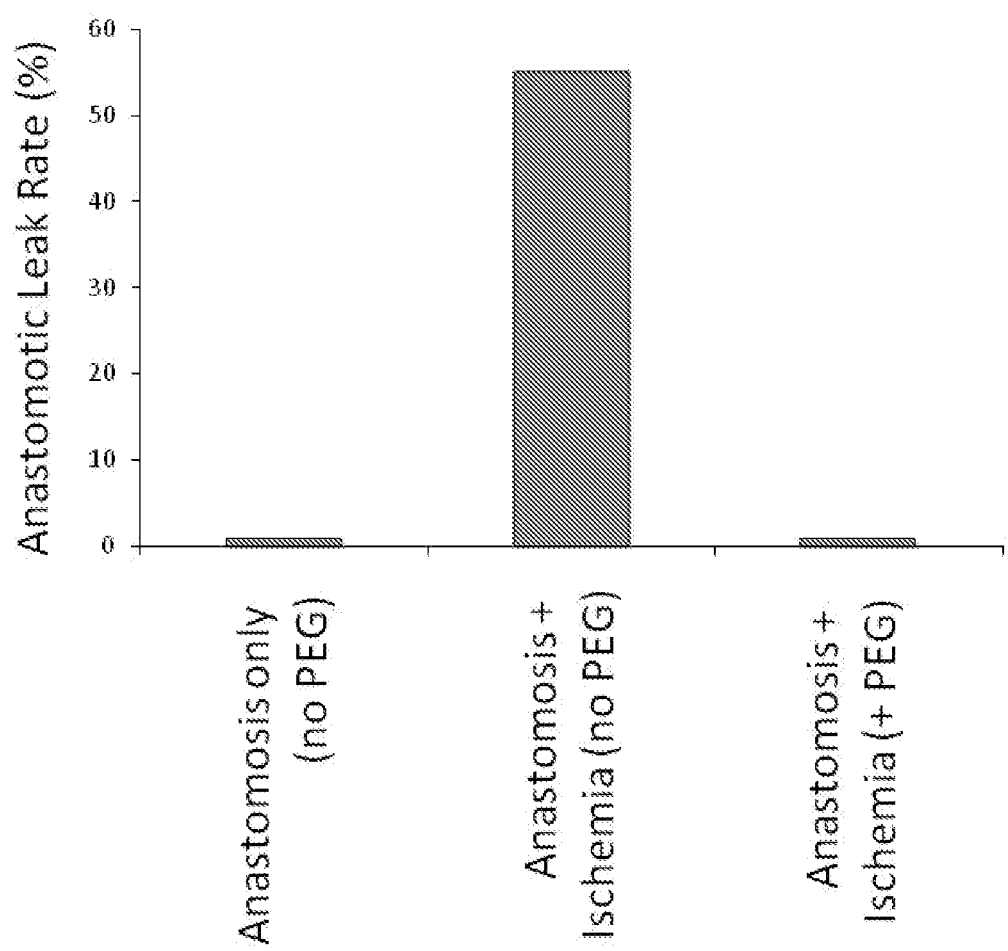
FIG. 14. Protective effect of PEG/Pi in rats. The figure illustrates that PEG/Pi prevents anastomotic leak in rats with ischemia.

The results of this example (depicted in FIG. 14) demonstrate that PEG/Pi is effective at preventing the anastomotic leak in an organism that has experienced an ischemic event in combination with anastomosis.

REFERENCES

1. Roos D, Dijksman L M, Oudemans-van Straaten H M, de Wit L T, Gouma D J, et al. Randomized clinical trial of perioperative selective decontamination of the digestive tract versus placebo in elective gastrointestinal surgery. Br J Surg 98: 1365-1372.
2. Merkel S, Wang W Y, Schmidt O, Dworak O, Wittekind C, et al. (2001) Locoregional recurrence in patients with anastomotic leakage after anterior resection for rectal carcinoma. Colorectal Dis 3: 154-160.
3. Lin J K, Yueh T C, Chang S C, Lin C C, Lan Y T, et al. The influence of fecal diversion and anastomotic leakage on survival after resection of rectal cancer. J Gastrointest Surg 15: 2251-2261.
4. Cohn I, Jr., Rives J D (1955) Antibiotic protection of colon anastomoses. Ann Surg 141: 707-717.
5. Schardey H M, Kamps T, Rau H G, Gatermann S, Baretton G, et al. (1994) Bacteria: a major pathogenic factor for anastomotic insufficiency. Antimicrob Agents Chemother 38: 2564-2567.
6. Schardey H M, Joosten U, Finke U, Staubach K H, Schauer R, et al. (1997) The prevention of anastomotic leakage after total gastrectomy with local decontamination. A prospective, randomized, double-blind, placebo-controlled multicenter trial. Ann Surg 225: 172-180.
7. Cohen S R, Cornell C N, Collins M H, Sell J E, Blanc W A, et al. (1985) Healing of ischemic colonic anastomoses in the rat: role of antibiotic preparation. Surgery 97: 443-446.
8. Akiyoshi T, Ueno M, Fukunaga Y, Nagayama S, Fujimoto Y, et al. (2011) Incidence of and risk factors for anastomotic leakage after laparoscopic anterior resection with intracorporeal rectal transection and double-stapling technique anastomosis for rectal cancer. Am J Surg 202: 259-264.
9. Choi D H, Hwang J K, Ko Y T, Jang H J, Shin H K, et al. (2010) Risk factors for anastomotic leakage after laparoscopic rectal resection. J Korean Soc Coloproctol 26: 265-273.
10. Zaborin A, Romanowski K, Gerdes S, Holbrook C, Lepine F, et al. (2009) Red death in *Caenorhabditis elegans* caused by *Pseudomonas aeruginosa* PAO1. Proc Natl Acad Sci USA 106: 6327-6332.
11. Romanowski K, Zaborin A, Fernandez H, Poroyko V, Valuckaite V, et al. Prevention of siderophore—mediated gut—derived sepsis due to *P. aeruginosa* can be achieved without iron provision by maintaining local phosphate abundance: role of pH. BMC Microbiol 11: 212.
12. Zaborina O, Kohler J E, Wang Y, Bethel C, Shevchenko O, et al. (2006) Identification of multi-drug resistant *Pseudomonas aeruginosa* clinical isolates that are highly disruptive to the intestinal epithelial barrier. Ann Clin Microbiol Antimicrob 5: 14.
13. Tremblay J, Deziel E (2008) Improving the reproducibility of *Pseudomonas aeruginosa* swarming motility assays. J Basic Microbiol 48: 509-515.
14. Zaborina O, Lepine F, Xiao G, Valuckaite V, Chen Y, et al. (2007) Dynorphin activates quorum sensing quinolone signaling in *Pseudomonas aeruginosa*. PLoS Pathog 3: e35.
15. Chevreux B, Pfisterer T, Drescher B, Driesel A J, Muller W E, et al. (2004) Using the miraEST assembler for reliable and automated mRNA transcript assembly and SNP detection in sequenced ESTs. Genome Res 14: 1147-1159.
16. Klockgether J, Munder A, Neugebauer J, Davenport C F, Stanke F, et al. Genome diversity of *Pseudomonas aeruginosa* PAO1 laboratory strains. J Bacteriol 192: 1113-1121.
17. Stover C K, Pham X Q, Erwin A L, Mizoguchi S D, Warrener P, et al. (2000) Complete genome sequence of *Pseudomonas aeruginosa* PAO1, an opportunistic pathogen. Nature 406: 959-964.
18. Lesic B, Rahme L G (2008) Use of the lambda Red recombinase system to rapidly generate mutants in *Pseudomonas aeruginosa*. BMC Mol Biol 9: 20.
19. Kohler T, Epp S F, Curty L K, Pechere J C (1999) Characterization of MexT, the regulator of the MexE-MexF-OprN multidrug efflux system of *Pseudomonas aeruginosa*. J Bacteriol 181: 6300-6305.
20. Aziz R K, Bartels D, Best A A, DeJongh M, Disz T, et al. (2008) The RAST Server: rapid annotations using subsystems technology. BMC Genomics 9: 75.
21. Tian Z X, Fargier E, Mac Aogain M, Adams C, Wang Y P, et al. (2009) Transcriptome profiling defines a novel regulon modulated by the LysR-type transcriptional regulator MexT in *Pseudomonas aeruginosa*. Nucleic Acids Res 37: 7546-7559.
22. Tian Z X, Mac Aogain M, O'Connor H F, Fargier E, Mooij M J, et al. (2009) MexT modulates virulence determinants in *Pseudomonas aeruginosa* independent of the MexEF-OprN efflux pump. Microb Pathog 47: 237-241.
23. Valuckaite V, Zaborina O, Long J, Hauer-Jensen M, Wang J, et al. (2009) Oral PEG 15-20 protects the intestine against radiation: role of lipid rafts. Am J Physiol Gastrointest Liver Physiol 297: G1041-1052.
24. Alanezi K, Urschel J D (2004) Mortality secondary to esophageal anastomotic leak. Ann Thorac Cardiovasc Surg 10: 71-75.
25. Blewett C J, Miller J D, Young J E, Bennett W F, Urschel J D (2001) Anastomotic leaks after esophagectomy for esophageal cancer: a comparison of thoracic and cervical anastomoses. Ann Thorac Cardiovasc Surg 7: 75-78.
26. Hyman N, Manchester T L, Osler T, Burns B, Cataldo P A (2007) Anastomotic leaks after intestinal anastomosis: it's later than you think. Ann Surg 245: 254-258.
27. Ricciardi R, Roberts P L, Marcello P W, Hall J F, Read T E, et al. (2009) Anastomotic leak testing after colorectal resection: what are the data? Arch Surg 144: 407-411; discussion 411-402.
28. Seal J B, Morowitz M, Zaborina O, An G, Alverdy J C (2010) The molecular Koch's postulates and surgical infection: a view forward. Surgery 147: 757-765.
29. Roos D, Dijksman L M, Oudemans-van Straaten H M, de Wit L T, Gouma D J, et al. (2011) Randomized clinical 30. Wu L, Estrada O, Zaborina O, Bains M, Shen L, et al. (2005) Recognition of host immune activation by *Pseudomonas aeruginosa*. Science 309: 774-777.
31. Zaborin A, Gerdes S, Holbrook C, Liu D C, Zaborina O Y, et al. (2012) *Pseudomonas aeruginosa* overrides the virulence inducing effect of opioids when it senses an abundance of phosphate. PLoS One 7: e34883.
32. Maseda H, Saito K, Nakajima A, Nakae T (2000) Variation of the mexT gene, a regulator of the MexEF-oprN efflux pump expression in wild-type strains of *Pseudomonas aeruginosa*. FEMS Microbiol Lett 192: 107-112.
33. Zaoui C, Overhage J, Lons D, Zimmermann A, Musken M, et al. An orphan sensor kinase controls quinolone signal production via MexT in *Pseudomonas aeruginosa*. Mol Microbiol 83: 536-547.
34. Jin Y, Yang H, Qiao M, Jin S MexT regulates the type III secretion system through MexS and PtrC in *Pseudomonas aeruginosa*. J Bacteriol 193: 399-410.
35. Kohler T, van Delden C, Curty L K, Hamzehpour M M, Pechere J C (2001) Overexpression of the MexEF-OprN multidrug efflux system affects cell-to-cell signaling in *Pseudomonas aeruginosa*. J Bacteriol 183: 5213-5222.
36. Maseda H, Uwate M, Nakae T (2010) Transcriptional regulation of the mexEF-oprN multidrug efflux pump operon by MexT and an unidentified repressor in nfxC-type mutant of *Pseudomonas aeruginosa*. FEMS Microbiol Lett 311: 36-43.

Each of the references cited herein is incorporated by reference in its entirety, or as relevant in view of the context of the citation.

From the disclosure provided herein it will be appreciated that, although specific embodiments of the invention have been described herein for purposes of illustration, various modifications may be made without deviating from the spirit and scope of the invention.

What is claimed is:

1. A method of treating anastomotic leakage comprising administering a therapeutically effective amount of a composition comprising a synthetic nanonet structure of phosphorylated high molecular weight polyethylene glycol of at least 8,000 daltons.

2. The method according to claim 1 wherein the anastomotic leakage is in the intestine or in the esophagus.

3. The method according to claim 1 wherein the phosphorylated high molecular weight polyethylene glycol has an average molecular weight selected from the group consisting of at least 10,000 daltons, at least 11,000 daltons, at least 12,000 daltons, at least 15,000 daltons and between 15,000 to 20,000 daltons.

4. The method according to claim 1 wherein a cause of the anastomotic leakage is a virulent *Pseudomonas aeruginosa*.

5. The method according to claim 4 wherein the virulent *Pseudomonas aeruginosa* has a loss-of-function mutation in mexT.

6. A method of treating anastomosis comprising administering a therapeutically effective amount of a composition comprising a synthetic nanonet structure of phosphorylated high molecular weight polyethylene glycol compound, wherein the phosphorylated high molecular weight polyethylene glycol compound is at least 8,000 daltons, thereby treating anastomosis by reducing the risk of an anastomotic leak.

7. The method according to claim 6 wherein the phosphorylated high molecular weight polyethylene glycol has an average molecular weight selected from the group consisting of at least 10,000 daltons, at least 11,000 daltons, at least 12,000 daltons, at least 15,000 daltons and between 15,000 to 20,000 daltons.

8. The method according to claim 6 wherein a cause of the anastomotic leakage is a virulent *Pseudomonas aeruginosa*.

9. A method of inhibiting the virulence of an intestinal pathogen in a patient at risk of having an anastomosis comprising administering an effective amount of a synthetic nanonet structures of phosphorylated high molecular weight polyethylene glycol, wherein the phosphorylated high molecular weight PEG has an average molecular weight selected from the group consisting of at least 10,000 daltons, at least 11,000 daltons, at least 12,000 daltons, at least 15,000 daltons and between 15,000 to 20,000 daltons.

10. The method according to claim 9 wherein the anastomosis is an intestinal anastomosis or an esophageal anastomosis.

11. A method of reducing the frequency of anastomotic leak in a subject comprising administering an effective amount of a synthetic nanonet structure of phosphorylated high molecular weight polyethylene glycol of at least 8,000 daltons to subjects known to have or to be at risk of having an anastomosis, wherein the phosphorylated high molecular weight PEG has an average molecular weight selected from the group consisting of at least 10,000 daltons, at least 11,000 daltons, at least 12,000 daltons, at least 15,000 daltons and between 15,000 to 20,000 daltons.

12. The method according to claim 11 wherein the subject has an intestinal anastomosis or an esophageal anastomosis.

13. The method according to claim 6 wherein the phosphorylated high molecular weight polyethylene glycol compound is administered prior to intestinal surgery.

* * * * *

UNITED STATES PATENT AND TRADEMARK OFFICE
CERTIFICATE OF CORRECTION

PATENT NO. : 9,937,199 B2
APPLICATION NO. : 14/421762
DATED : April 10, 2018
INVENTOR(S) : John C. Alverdy Page 1 of 1

It is certified that error appears in the above-identified patent and that said Letters Patent is hereby corrected as shown below:

In the Claims

Column 28, Line 15, "structures" should read -- structure --.

Signed and Sealed this
Twenty-eighth Day of August, 2018

Andrei Iancu
*Director of the United States Patent and Trademark Office*

SEQUENCE LISTING

```
<160> NUMBER OF SEQ ID NOS: 13

<210> SEQ ID NO 1
<211> LENGTH: 916
<212> TYPE: DNA
<213> ORGANISM: Homo sapiens
<220> FEATURE:
<221> NAME/KEY: misc_feature
<222> LOCATION: (1)..(916)
<223> OTHER INFORMATION: mexTP1 open reading frame

<400> SEQUENCE: 1
catgaaccga aacgacctgc gccgcgtcga tctgaacctg ctgatcgtgt tcgagaccct      60
gatgcacgaa cgcagcgtga cccgcgccgc agagaaactg ttcctcggcc agccggccat     120
cagcgccgcg ctgtcgcgcc tgcgcacgct gttcgacgac ccgctgttcg tccgtaccgg     180
acgcagcatg gagcccaccg cgcgagccca ggaaatcttc gcccacctgt cgccggcgct     240
ggattccatc tccaccgcca tgagtcgcgc cagcgagttc gatccggcga ccagcaccgc     300
ggtgttccgc atcggccttt ccgacgacgt cgagttcggc ctgttgccgc ccctgctccg     360
ccgcctgcgc gcggaggcgc cggggatcgt cctcgtcgtg cgccgcgcca actatctatt     420
gatgccgaac ctgctggcct cggggagat ctcggtgggc gtcagctaca ccgacgaact     480
gccggccaac gccaagcgca agaccgtgcg ccgcagcaag ccgaagatcc tccgcgccga     540
ctccgcgccc ggccagctga ccctcgacga ctattgcgcg cgaccgcacg cgctggtgtc     600
cttcgccggc gacctcagcg gcttcgtcga cgaggagctg gaaaaattcg gccgcaagcg     660
caaggtggtc ctggcggtgc cgcagttcaa cggcctcggc accctcctgg ccggcaccga     720
catcatcgcc accgtgcccg actacgccgc ccaggcgctg atcgccgccg gcggcctacg     780
cgccgaggac ccaccgttcg agacccgggc cttcgaactg tcgatggctt ggcgcggcgc     840
ccaggacaac gatccggccg aacgctggct gcgctcgcgg atcagcatgt tcatcggcga     900
tccggacagt ctctga                                                     916

<210> SEQ ID NO 2
<211> LENGTH: 304
<212> TYPE: PRT
<213> ORGANISM: Homo sapiens
<220> FEATURE:
<221> NAME/KEY: MISC_FEATURE
```

<222> LOCATION: (1)..(304)
<223> OTHER INFORMATION: MexTP1 protein sequence

<400> SEQUENCE: 2

Met Asn Arg Asn Asp Leu Arg Arg Val Asp Leu Asn Leu Leu Ile Val
1               5                   10                  15

Phe Glu Thr Leu Met His Glu Arg Ser Val Thr Arg Ala Ala Glu Lys
            20                  25                  30

Leu Phe Leu Gly Gln Pro Ala Ile Ser Ala Ala Leu Ser Arg Leu Arg
        35                  40                  45

Thr Leu Phe Asp Asp Pro Leu Phe Val Arg Thr Gly Arg Ser Met Glu
    50                  55                  60

Pro Thr Ala Arg Ala Gln Glu Ile Phe Ala His Leu Ser Pro Ala Leu
65                  70                  75                  80

Asp Ser Ile Ser Thr Ala Met Ser Arg Ala Ser Glu Phe Asp Pro Ala
                85                  90                  95

Thr Ser Thr Ala Val Phe Arg Ile Gly Leu Ser Asp Asp Val Glu Phe
            100                 105                 110

Gly Leu Leu Pro Pro Leu Leu Arg Arg Leu Arg Ala Glu Ala Pro Gly
        115                 120                 125

Ile Val Leu Val Val Arg Arg Ala Asn Tyr Leu Leu Met Pro Asn Leu
    130                 135                 140

Leu Ala Ser Gly Glu Ile Ser Val Gly Val Ser Tyr Thr Asp Glu Leu
145                 150                 155                 160

Pro Ala Asn Ala Lys Arg Lys Thr Val Arg Arg Ser Lys Pro Lys Ile
                165                 170                 175

Leu Arg Ala Asp Ser Ala Pro Gly Gln Leu Thr Leu Asp Asp Tyr Cys
            180                 185                 190

Ala Arg Pro His Ala Leu Val Ser Phe Ala Gly Asp Leu Ser Gly Phe
        195                 200                 205

Val Asp Glu Glu Leu Gly Lys Phe Gly Arg Lys Arg Lys Val Val Leu
    210                 215                 220

Ala Val Pro Gln Phe Asn Gly Leu Gly Thr Leu Leu Ala Gly Thr Asp
225                 230                 235                 240

Ile Ile Ala Thr Val Pro Asp Tyr Ala Ala Gln Ala Leu Ile Ala Ala
                245                 250                 255

Gly Gly Leu Arg Ala Glu Asp Pro Pro Phe Glu Thr Arg Ala Phe Glu
            260                 265                 270

Leu Ser Met Ala Trp Arg Gly Ala Gln Asp Asn Asp Pro Ala Glu Arg
        275                 280                 285

Trp Leu Arg Ser Arg Ile Ser Met Phe Ile Gly Asp Pro Asp Ser Leu
    290                 295                 300

<210> SEQ ID NO 3
<211> LENGTH: 916
<212> TYPE: DNA
<213> ORGANISM: Homo sapiens
<220> FEATURE:
<221> NAME/KEY: misc_feature
<222> LOCATION: (1)..(916)
<223> OTHER INFORMATION: mexT P2

<400> SEQUENCE: 3
catgaaccga aacgacctgc gccgcgtcga tctgaacctg ctgatcgtgt tcgagaccct    60
gatgcacgaa cgcagcgtga cccgcgccgc agagaaactg ttcctcggcc agccggccat   120
cagcgccgcg ctgtagcgcc tgcgcacgct gttcgacgac ccgctgttcg tccgtaccgg   180

```
acgcagcatg gagcccaccg cgcgagccca ggaaatcttc gcccacctgt cgccggcgct    240
ggattccatc tccaccgcca tgagtcgcgc cagcgagttc gatccggcga ccagcaccgc    300
ggtgttccgc atcggccttt ccgacgacgt cgagttcggc ctgttgccgc ccctgctccg    360
ccgcctgcgc gcggaggcgc cggggatcgt cctcgtcgtg cgccgcgcca actatctatt    420
gatgccgaac ctgctggcct cgggggagat ctcggtgggc gtcagctaca ccgacgaact    480
gccggccaac gccaagcgca agaccgtgcg ccgcagcaag ccgaagatcc tccgcgccga    540
ctccgcgccc ggccagctga ccctcgacga ctattgcgcg cgaccgcacg cgctggtgtc    600
cttcgccggc gacctcagcg gcttcgtcga cgaggagctg gaaaaattcg gccgcaagcg    660
caaggtggtc ctggcggtgc cgcagttcaa cggcctcggc accctcctgg ccggcaccga    720
catcatcgcc accgtgcccg actacgccgc ccaggcgctg atcgccgccg gcggcctacg    780
cgccgaggac ccaccgttcg agacccgggc cttcgaactg tcgatggctt ggcgcggcgc    840
ccaggacaac gatccggccg aacgctggct gcgctcgcgg atcagcatgt tcatcggcga    900
tccggacagt ctctga                                                   916
```

```
<210> SEQ ID NO 4
<211> LENGTH: 44
<212> TYPE: PRT
<213> ORGANISM: Homo sapiens
<220> FEATURE:
<221> NAME/KEY: MISC_FEATURE
<222> LOCATION: (1)..(44)
<223> OTHER INFORMATION: MexTP2 truncated

<400> SEQUENCE: 4

Met Asn Arg Asn Asp Leu Arg Arg Val Asp Leu Asn Leu Leu Ile Val
1               5                   10                  15

Phe Glu Thr Leu Met His Glu Arg Ser Val Thr Arg Ala Ala Glu Lys
            20                  25                  30

Leu Phe Leu Gly Gln Pro Ala Ile Ser Ala Ala Leu
        35                  40

<210> SEQ ID NO 5
<211> LENGTH: 8
<212> TYPE: DNA
<213> ORGANISM: Homo sapiens
<220> FEATURE:
<221> NAME/KEY: misc_feature
<222> LOCATION: (1)..(8)
<223> OTHER INFORMATION: Sequence of eight base pair insertion in mexT
      of nfx-C strains of Pseudomonas aeruginosa.

<400> SEQUENCE: 5 cggccagc                                                              8

<210> SEQ ID NO 6
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 6
acggccgacc                                                           10

<210> SEQ ID NO 7
<211> LENGTH: 10
<212> TYPE: DNA
```

```
<213> ORGANISM: Artificial sequence
<220> FEATURE:
<223> OTHER INFORMATION: Synthetic oligonucleotide

<400> SEQUENCE: 7
agcgggccaa                                                                  10

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide -- Forward primer for
      amplifying entire coding region of mexT from MPA01

<400> SEQUENCE: 8
cggataatga tcgggggtat                                                       20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide -- reverse primer for
      amplifying entire coding region of mexT from MPA01

<400> SEQUENCE: 9
ccgaattttt ccagctcctc                                                       20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide -- Forward primer for
      verifying transformants for correct PCR insertion

<400> SEQUENCE: 10
gcctgtcagt gatcctatgc                                                       20

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide -- Reverse primer for
      verifying transformants for correct PCR insertion

<400> SEQUENCE: 11
gatcgccgat gaacatgc                                                         18

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide -- Forward primer for
      direct sequencing of amplified mexT in the P1 and P2 strains

<400> SEQUENCE: 12
gcctgtcagt gatcctatgc                                                       20

<210> SEQ ID NO 13
<211> LENGTH: 18
<212> TYPE: DNA
<213> ORGANISM: Artificial sequence
<220> FEATURE:
```

```
<223> OTHER INFORMATION: Synthetic oligonucleotide -- Reverse primer for
      direct sequencing of amplified mexT in the P1 and P2 strains

<400> SEQUENCE: 13
gatcgccgat gaacatgc                                                    18
```